United States Patent  
Costa et al.

(10) Patent No.: US 6,421,553 B1
(45) Date of Patent: Jul. 16, 2002

(54) SPECTRAL DATA CLASSIFICATION OF SAMPLES

(75) Inventors: Peter J. Costa, Hudson; Kwong Hui, Woburn; Robert J. Nordstrom, Hanover, all of MA (US)

(73) Assignee: MediaSpectra, Inc., Lexington, MA (US)

( * ) Notice: Subject to any disclaimer, the term of this patent is extended or adjusted under 35 U.S.C. 154(b) by 12 days.

(21) Appl. No.: 09/738,481

(22) Filed: Dec. 15, 2000

Related U.S. Application Data

(63) Continuation-in-part of application No. 09/470,071, filed on Dec. 22, 1999.
(60) Provisional application No. 60/113,761, filed on Dec. 23, 1998.

(51) Int. Cl.$^7$ .................................................. A61B 6/00
(52) U.S. Cl. ....................... 600/476; 600/473; 600/477; 356/302; 356/303
(58) Field of Search ................................ 600/473, 476, 600/477; 356/302, 303, 306

(56) References Cited

U.S. PATENT DOCUMENTS

| | | | | |
|---|---|---|---|---|
| 5,599,717 A | * | 2/1997 | Vo-Dinh | 436/171 |
| 5,938,617 A | * | 8/1999 | Vo-Dinh | 436/171 |
| 6,091,985 A | * | 7/2000 | Alfano et al. | 436/172 |
| 6,208,887 B1 | * | 3/2001 | Clarke | 356/301 |

* cited by examiner

*Primary Examiner*—Marvin M. Lateef
*Assistant Examiner*—Runa Shah Qaderi
(74) *Attorney, Agent, or Firm*—Testa, Hurwitz & Thibeault, LLP

(57) ABSTRACT

A system and method for classifying tissue by application of discriminant analysis to spectral data. Spectra are recorded as amplitudes at a series of discrete wavelengths. Pluralities of reference spectra are recorded for specimens having known conditions. The reference spectra are subjected to discriminant analysis to determine wavelength regions of interest for the analysis. A plurality of amplitudes are selected for the analysis, and are plotted in an N-dimensional space. For each plurality of reference spectra corresponding to a specific known condition, a characteristic point is determined and plotted, the characteristic point representative of the known condition. A test spectrum is recorded from a test specimen, and the plurality of amplitudes corresponding in wavelength to the wavelength regions of interest are selected. A characteristic point in N-dimensional space is determined for the test spectrum. The distance of the characteristic point of the test spectrum from each of the plurality of characteristic points representative of known conditions is determined. The test specimen is assigned the condition corresponding to the characteristic point of a plurality of reference spectra, based on a distance relationship with at least two distances, provided that at least one distance is less than a pre-determined maximum distance. In some embodiments, the test specimen can comprise human cervical tissue, and the known conditions can include normal health, metaplasia, CIN I and CIN II/III.

29 Claims, 15 Drawing Sheets

SPECTRAL DATA CLASSIFICATION OF SAMPLES

CROSS-REFERENCE TO RELATED APPLICATIONS

This application is a continuation-in-part of U.S. patent application Ser. No. 09/470,071, filed Dec. 22, 1999, which claims priority to and the benefit of U.S. provisional patent application Ser. No. 60/113,761, filed Dec. 23, 1998, and this application is related to the U.S. patent application Ser. No. 09/738,612 entitled, "System for Normalizing Spectra" and filed on even date herewith, and to the U.S. patent application Ser. No. 09/738,612 entitled, "A Spectroscopic System Employing A Plurality of Data Types" and filed on even date herewith. All of the above applications are assigned to the common assignee of this application, and are hereby incorporated by reference.

GOVERNMENT RIGHTS

This invention was made with government support under Contract No. CA6648 1 awarded by National Cancer Institute, NIH The government may have certain rights in the invention.

FIELD OF THE INVENTION

This invention relates generally to the use of spectral data for categorizing materials. More particularly, the invention relates to the use of spectral data for classifying tissue by discriminant analysis.

1. Field of the Invention

This invention relates generally to the use of spectral data for categorizing materials. More particularly, the invention relates to the use of spectral data for classifying tissue by discriminant analysis.

2. Background of the Invention

Information obtained from spectral analysis is useful in such diverse fields as geology, chemistry, medicine, physics and biology. For example, it is known that cells and tissues emit characteristic spectra in response to light stimulation. The nature of those spectra is indicative of the health of the tissue. Thus, a cancerous tissue has associated with it an emission spectrum that is different than the emission spectrum of a corresponding healthy tissue. Similarly, emission spectra are used in attempts to differentiate between the mineral content of two or more geologic samples.

In any spectral analysis of a sample, the condition of which is unknown, an attempt is made to associate the sample with a reference sample that represents a known state. Commonly, spectral values such as amplitude measured in response to excitation, are used to place a test sample on a range of spectral values obtained from samples of known condition. The object is to identify a best fit between the test sample and a sample the condition of which is known. While such an analysis is straightforward in principle, it is often the case that a spectrum recorded from a test specimen does not match any known spectrum, or appears to have features present in more than one known spectrum. In addition, there are often multiple features of interest or of consequence in a single spectrum, which makes any comparison problematic. Thus, it is not always clear where a test sample should be placed with a range of known samples. the result is that the spectra of many samples cannot be assigned a condition by comparison to known samples without significant ambiguity.

SUMMARY OF THE INVENTION

In spectral analysis, different types of spectra provide distinct and useful kinds of information. In conventional spectroscopic analysis, one may employ such diverse methods and techniques as optical spectra spanning the infrared, visible and ultraviolet based on the interactions of materials with light (or electromagnetic radiation), spectroscopic methods based on electromagnetic resonance, such as electron spin resonance (esr) and nuclear magnetic resonance (nmr) spectroscopy, x-ray spectroscopic methods based on crystal structures, Moessbauer spectroscopy based on nuclear resonance, and Raman spectroscopy based on molecular dynamics. Often, to characterize a specimen as completely as possible, all of the above methods are employed, irrespective of the results of a particular method of analysis, and the totality of the results obtained are used to analyze or describe the specimen being examined. In the present inventive systems and methods, a first spectral result is used to determine whether a specimen being tested can be categorized, and if the initial result warrants further analysis, as when a categorization cannot be made in a definitive manner, a further specific analysis is performed in an attempt to obtain suitable categorization information. In some instances, it is impossible to reach a definitive conclusion.

The invention provides methods of comparing spectral data from a test sample with spectral data corresponding to known conditions. In particular, the invention provides methods for assigning at least one condition to a test sample based upon a relationship between at least two metrics, each representative of the similarity of the test sample to samples having known conditions, based upon a comparison of spectral data from the test sample to a constellation of reference data from the samples having known conditions. For a known condition, one can record and analyze reference spectra from a number of specimens having the known condition to provide a number of reference data points characteristic of that known condition. N-dimensional data points obtained from reference spectra for a plurality of specimens exhibiting the same condition tend to fall in a cluster, or constellation.

In one aspect, the invention provides a method for determining a condition of a test specimen. A preferred method comprises obtaining at least one optical spectrum from a test specimen, the optical spectrum being characterized by (N) quantitative features, each of the (N) quantitative features corresponding to one of (N) pre-selected wavelengths, wherein (N) is an integer greater than 1. Preferred methods further comprise determining a first metric between a point in N-dimensional space corresponding to the (N) quantitative features of the optical spectrum from the test specimen and a point in N-dimensional space characteristic of a first constellation of reference data that includes a first plurality of points in N-dimensional space, each of which corresponds to (N) quantitative features of a reference optical spectrum at the (N) pre-selected wavelengths, the first constellation of reference data being representative of a first known condition. Preferred methods further comprise determining a second metric between the point in N-dimensional space corresponding to the (N) quantitative features of the optical spectrum from the test specimen and a point in N-dimensional space characteristic of a second constellation of reference data that includes a second plurality of points in N-dimensional space, each of which corresponds to (N) quantitative features of a reference optical spectrum at the (N) pre-selected wavelengths, the second constellation of reference data being representative of a second known condition. Preferred methods further comprise assigning one of the first and the second conditions to the test specimen, based at least in part on a relationship between the first and the second metrics.

In one embodiment, the first metric and the second metric are each selected from the group consisting of a square root of a sum of the squares of the differences in coordinates of points in the N-dimensional space, a Mahalanobis distance, a Bhattacharyya distance, and a probability.

In another embodiment, methods of the invention further comprise analyzing biological tissue. Preferred methods comprise obtaining at least one optical spectrum from a tissue sample obtained form a patient, and determining a first metric by comparing optical features of the spectrum obtained from the tissue sample to a first constellation of data points representing spectral characteristics of a first condition; determining a second metric by comparing optical features of the spectrum obtained from the tissue sample to a second constellation of data points representing spectral characteristics of a second condition; and assigning one of the two conditions to the test sample based upon a relationship between the first and second metrics. In a preferred embodiment, the optical spectra obtained are selected from the group consisting of a fluorescence spectrum, a reflectance spectrum and a Raman spectrum. In one embodiment, the tissue specimen is human cervical tissue or a sample prepared from human cervical tissue. In one embodiment, methods of the invention are conducted in vivo. In a preferred embodiment, the first condition is normal health and the second condition is selected from the group consisting of moderate cervical intraepithelial neoplasia (CIN II) and severe cervical intraepithelial neoplasia (CIN III).

In one embodiment, the method further includes reporting that the optical spectrum is inconclusive with regard to the first known condition and the second known condition in response to each of the first and the second metrics exceeding a pre-determined metric value. In one embodiment, at least one of the points in N-dimensional space characteristic of a first constellation of reference data and the point in N-dimensional space characteristic of a second constellation of reference data is selected from the group consisting of a centroid of a respective one of the constellations of reference data and a weighted average of a respective one of the constellations of reference data. In one embodiment, the quantitative features are selected from the group consisting an amplitude, an average of a plurality of amplitudes, a function of a plurality of amplitudes, an average slope, a derivative, and an integral.

In another aspect, the invention provides a method of determining that a condition of a test specimen belongs to one of a plurality of known conditions, each of the plurality of conditions represented by a reference specimen constellation corresponding to a selected member of a plurality of known conditions. Preferred methods comprise obtaining at least one optical spectrum from a test specimen, and selecting (N) quantitative features from the spectrum, each of the (N) quantitative features being associated with one of (N) pre-selected wavelengths, wherein (N) is an integer greater than 1. Such methods further comprise determining a plurality of metric values, each metric value corresponding to a measure between a point in the N-dimensional space corresponding to the (N) quantitative features of the optical spectrum from the test spectrum and a point in N-dimensional space characteristic of a constellation of reference data representing one of a plurality of known conditions, each the constellations including a plurality of points in the N-dimensional space. Finally, such methods comprise determining a condition to be ascribed to the test specimen based at least in part on the relation between the plurality of metric values.

In one embodiment, at least one of the plurality of metrics described above is a distance, the distance being calculated based on a square root of a sum of the squares of the differences in the corresponding coordinates in the N-dimensional space, a Mahalanobis distance, or a Bhattacharyya distance. In one embodiment, at least one of the plurality of metrics is a probability.

In one embodiment, methods of the invention further comprise obtaining at least one optical spectrum from a biological sample obtained from a patient, and deducing one of a plurality of states of health to be ascribed to the sample based up a fluorescence spectrum, a reflectance spectrum or a Raman spectrum. In one embodiment, the sample is human cervical tissue. Also in a preferred embodiment, methods of the invention are conducted on cervical tissue in vivo. In the analysis of cervical tissue, the conditions used to assign a condition to the test sample are selected from the group consisting of normal squamous epithelium, columnar epithelium, immature metaplasia, mature metaplasia, Nabothian cysts, crypt openings, traumatically eroded tissue, benign polyps, mild cervical intraepithelial neoplasia (CIN I), moderate cervical intraepithelial neoplasia (CIN II), severe cervical intraepithelial neoplasia (CIN III) and cancer.

In one embodiment, the method further includes reporting that the optical spectrum is inconclusive with regard to the plurality of known conditions in response to each of the plurality of metrics exceeding a pre-determined metric value. In one embodiment, at least one of the points in N-dimensional space characteristic of a constellation of reference data representing one of a plurality of known conditions is selected from the group consisting of a centroid of a respective one of the constellations of reference data and a weighted average of a respective one of the constellation of reference data. In one embodiment, the quantitative features are selected from the group consisting of an amplitude, an average of a plurality of amplitudes, a function of a plurality of amplitudes, an average slope, a derivative, and an integral.

In still another aspect, the invention relates to a system for determining a condition of a test specimen. The system comprises a computer that receives data characteristic of at leas one optical spectrum recorded from a test specimen, the data comprising (N) quantitative features of the optical spectrum, each of the (N) quantitative features corresponding to one of (N) pre-selected wavelengths, wherein (N) is an integer greater than 1. The system further comprises a first memory in communication with the computer and containing a first constellation of reference data comprising a first plurality of points in N-dimensional space, each of the first plurality of points corresponding to (N) quantitative features of a reference optical spectrum at the (N) pre-selected wavelengths, the first constellation of reference data being representative of a first known condition. The system further comprised a second memory in communication with the computer that contains a second constellation of reference data comprising a second plurality of points in N-dimensional space, each of the second plurality of points corresponding to (N) quantitative features of a reference optical spectrum at the (N) pre-selected wavelengths, the second constellation of reference data being representative of a second known condition. The computer is adapted to determine first metric between a point in N-dimensional space corresponding to the (N) quantitative features of the optical spectrum from the test specimen and a point in N-dimensional space characteristic of the first constellation of reference data. The computer is further adopted to determine a second metric between the point in N-dimensional space corresponding to the (N) quantitative features of the optical spectrum from the test specimen and a point in N-dimensional space characteristic of the second constellation of reference data. Finally, the computer is adapted to assign one of the first and the second condition to the test specimen, based at least in part on a relationship between the first and the second metric values.

In one embodiment, the first distance and the second metrics each are selected from the group consisting of a square root of a sum of the squares of the differences in coordinated of points in the N-dimensional space, a Mahalanobis distance, and a Bhattacharyya distance. In one embodiment, the test specimen is a tissue sample and the first and the second conditions correspond to states of health. In one embodiment, the tissue sample is human cervical tissue, the first state of health and the second state of health are selected from normal health including normal squamous epithelium, columnar epithelium, immature metaplasia, mature metaplasia, Nabothian cysts, crypt opening, traumatically eroded tissue, benign polyps, mild cervical intraepithelial neoplasia (CIN I), moderated cervical intraepithelial neoplasia (CIN II), severe cervical intraepithelial neoplasia (CIN III) and cancer. In one embodiment, the computer is further adapted to report that the data characteristic of the optical spectrum recorded from the test specimen is inconclusive as regards the first known condition and the second known condition in response to the first and the second distances both exceeding a pre-determined metric. In another embodiment, the computer is further adapted to computer a centroid of a constellation of reference data comprising a point in N-dimensional space characteristic of a first constellation of reference data or a point in N-dimensional space characteristic of a second constellation of reference data. Preferably, the at least one optical spectrum recorded from a test specimen including an optical spectrum selected from a fluorescence spectrum, a reflectance spectrum and a Raman spectrum. In one embodiment, the point in N-dimensional space characteristic of a constellation of reference data representing one of a plurality of known conditions is selected from the group consisting of a centroid of the constellations of reference data and a weighted average of the constellation of reference data. In one embodiment, the test specimen is human tissue. In one embodiment, the first and the second known conditions are selected from the group consisting of healthy tissue, inflammation of tissue, atrophic tissue, hypoxic tissue, diseased tissue, and cancerous tissue.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DESCRIPTION OF THE ILLUSTRATIVE EMBODIMENT

The invention will be described in terms of embodiments that relate to the use of optical spectra to discriminate between known conditions, particularly in the area of medical diagnostics, and especially as it relates to the analysis of spectra obtained from human cervical tissue in the detection of cervical cancer. However, the invention has applicability generally in the area of using optical spectra to distinguish between two or more conditions.

Figure 1:
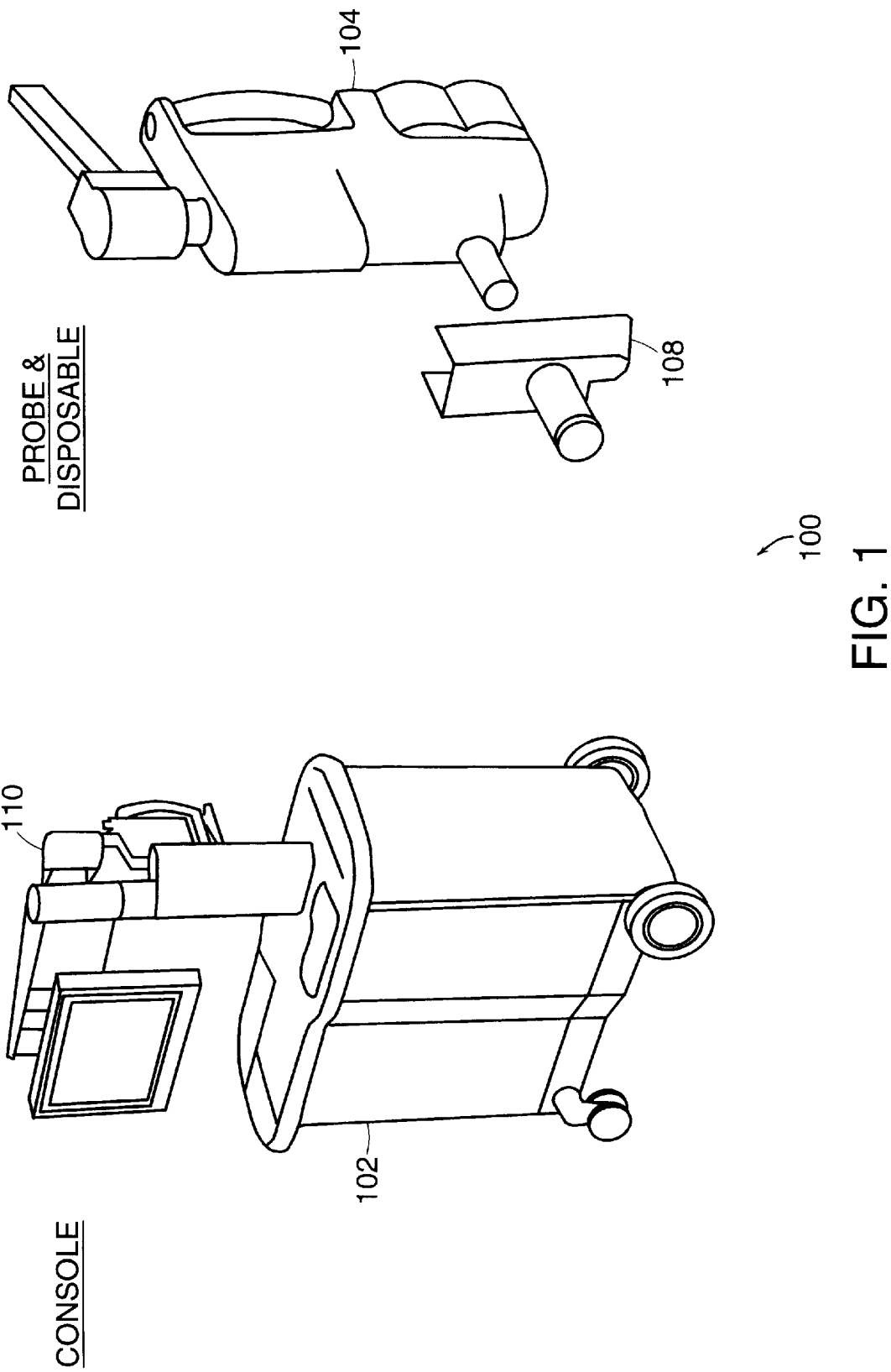
FIG. 1 shows an exemplary spectroscopic system employing a characterization method according to an illustrative embodiment of the invention.

FIG. 1 depicts an exemplary spectroscopic system 100 employing a spectral data classification method according to an illustrative embodiment of the invention. The spectroscopic system comprises a console 102 connected to a probe 104 by a cable 106. The cable 106 carries electrical and optical signals between the console 102 and the probe 104. The probe 104 accommodates a disposable component 108 which used only once, and discarded after such use. The console 102 and the probe 104 are mechanically connected by cable 106. The console 102 contains much of the hardware and the software of the system, and the probe 104 contains the necessary hardware for making suitable spectroscopic observations. The details of the system are further explained in conjunction with FIG. 2.

Figure 2:
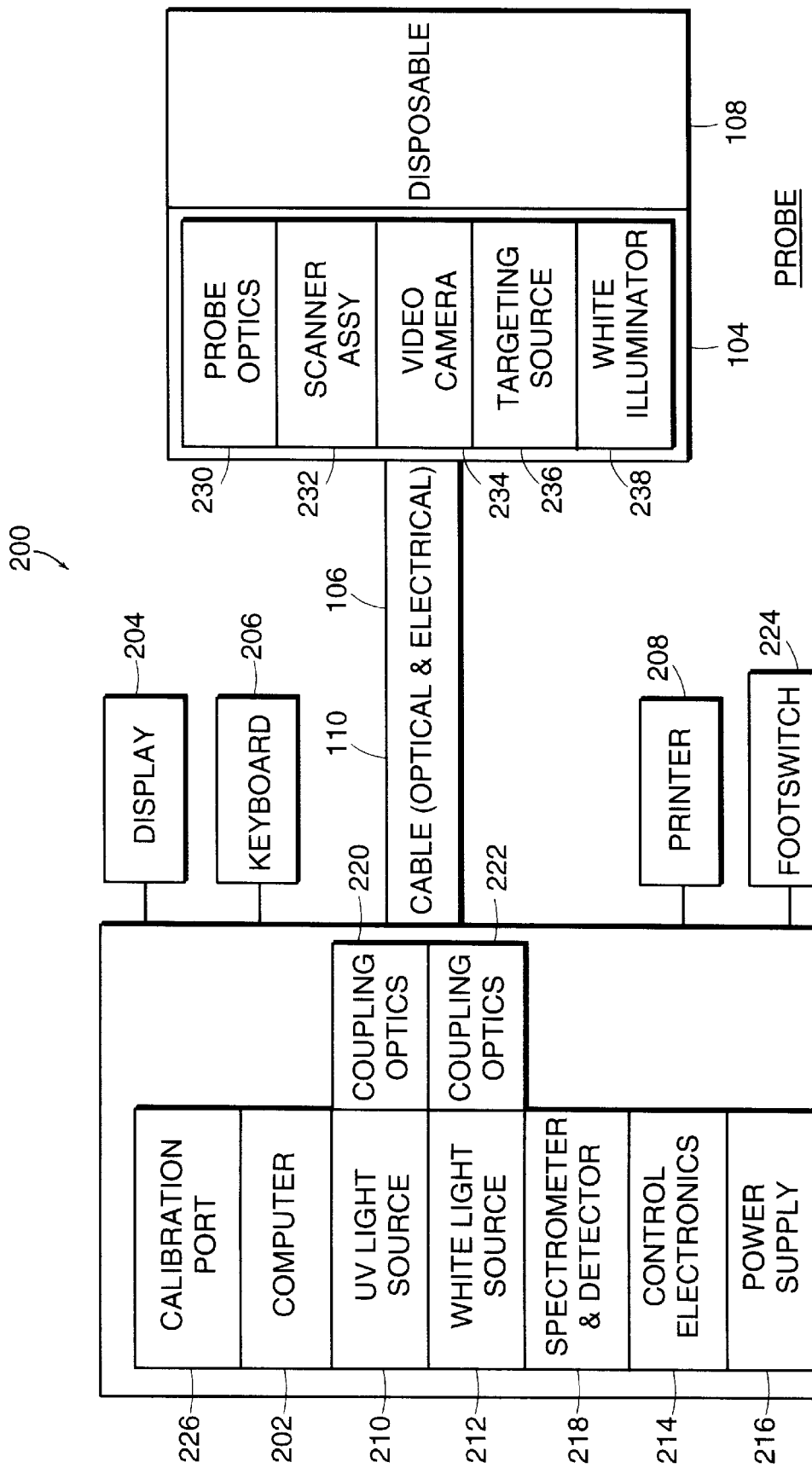
FIG. 2 shows an exemplary operational block diagram of the spectroscopic system of FIG. 1.

FIG. 2 shows an exemplary operational block diagram 200 of a spectroscopic system of the type depicted in FIG.

1. The console 102 comprises a computer 202 which executes software that controls the operation of the spectroscopic system 100. The software comprises one or more modules recorded on machine-readable media, which can be any medium, such as magnetic disks, magnetic tape, CD-ROM, semiconductor memory, or the like. Preferably, the machine-readable medium is resident within the computer 202. In alternative embodiments, the machine-readable medium is connected to the computer 202 by a communication link. In alternative embodiments, one can substitute computer instructions in the form of hardwired logic for software, or one can substitute firmware (i.e., computer instructions recorded on devices such as PROMs, EPROMS or EEPROMs, or the like) for software. The term machine-readable instructions as used herein is intended to encompass software, hardwired logic, firmware and the like.

The computer 202 is a general purpose computer. The computer 202 can be, for example, an embedded computer, or a personal computer such as a laptop or desktop computer, that is capable of running the software, issuing suitable control commands, and recording information in real time. The computer 202 comprises one or more machine-readable memories, such as semiconductor memory, magnetic memory, and/or optical memory that can be used to record and recover data. The computer 202 has a display 240 for reporting information to an operator of the spectroscopic system 100, a keyboard 206 for enabling the operator to enter information and commands, and a printer 208 for providing a print-out, or permanent record, of measurements made by the spectroscopic system 100 and for printing diagnostic results, for example, for inclusion in the chart of a patient. As described below in more detail, in an illustrative embodiment of the invention, some commands entered at the keyboard, enable a user to select particular segments of a spectrum for normalization. Other commands enable a user to select the wavelength range for each particular segment and to specify both wavelength contiguous and non-contiguous segments.

The console 102 also comprises an ultraviolet (UV) source 210 such as a nitrogen laser or a frequency-tripled Nd:YAG laser to excite fluorescence emission from a specimen, a white light source 212 such as one or more Xenon flash lamps to illuminate a specimen for reflectance measurements, and control electronics 214 for controlling the light sources both as to intensity and as to the time of onset of operation and the duration of operation. Other light sources can be provided in the console 102 such as lasers capable of initiating a Raman scattering from a specimen. One or more power supplies 216 are included in the console 102, to provide regulated power for the operation of all of the components. The console 102 also comprises at least one spectrometer and at least one detector (spectrometer and detector 218) suitable for use with each of the light sources. In some embodiments, a single spectrometer can operate with both the UV light source and the white light source. In some embodiments, the same detector can record UV and white light signals, and in some embodiments different detectors are used for each light source.

The console 102 also comprises coupling optics 220 to couple the UV illumination from the UV light source 210 to one or more optical fibers in the cable 106 for transmission to the probe 104, and for coupling the white light illumination from the white light source 212 to one or more optical fibers in the cable 106 for transmission to the probe 104. The console 102 also comprises coupling optics 222 to couple the spectral response of a specimen to UV illumination from the UV light source 210 observed by the probe 104 and carried by one or more optical fibers in the cable 106 for transmission to the spectrometer and detector 218, and for coupling the spectral response of a specimen to the white light illumination from the white light source 212 observed by the probe 104 and carried by one or more optical fibers in the cable 106 for transmission to the spectrometer and detector 218. The console 102 comprises a footswitch 224 to enable an operator of the spectroscopic system 100 to signal when it is appropriate to commence a spectral observation by stepping on the switch. In this manner, the operator has his or her hands free to perform other tasks, for example, aligning the probe 104.

The console 102 comprises a calibration port 226 for calibrating the optical components of the spectrometer system. The operator places the probe 104 in registry with the calibration port 226 and issues a command that starts the calibration operation. A light source of the system is used to expose one or more targets of known optical characteristics to obtain a calibration signal. Alternatively, a calibrated light source provides illumination of known intensity as a function of wavelength as a calibration signal. The probe 104 detects the calibration signal. The probe 104 transmits the detected signal through the optical fiber in the cable 106, through the coupling optics 222 to the spectrometer and detector 218. A test spectral result is obtained. A calibration of the spectral system is computed as the ratio of the amplitude of the known illumination at a particular wavelength divided by the test spectral result at the same wavelength.

The probe 104 comprises probe optics 230 for illuminating a specimen to be analyzed with UV and white light from the UV source 210 and the white light source 212, and for collecting the fluorescent and backscatter illumination from the specimen that is being analyzed. The probe comprises a scanner assembly 232 that provides illumination from the UV source 210 in a raster pattern over a target area of the specimen of cervical tissue to be analyzed. The probe comprises a video camera 234 for observing and recording visual images of the specimen under analysis. The probe 104 comprises a targeting source 236, which can be used to determine where on the surface of the specimen to be analyzed the probe 104 is pointing. The probe 104 also comprises a white light illuminator 238 to assist the operator in visualizing the specimen to be analyzed. Once the operator aligns the spectroscopic system and depresses the footswitch 224, the computer 202 controls the actions of the light sources 210, 212, the coupling optics 220, the transmission of light signals and electrical signals through the cable 106, the operation of the probe optics 230 and the scanner assembly 232, the retreival of observed spectra via the cable 106, the coupling of the observed spectra via the coupling optics 222 into the spectrometer and detector 218, the operation of the spectrometer and detector 218, and the subsequent signal processing and analysis of the recorded spectra.

Figure 3:
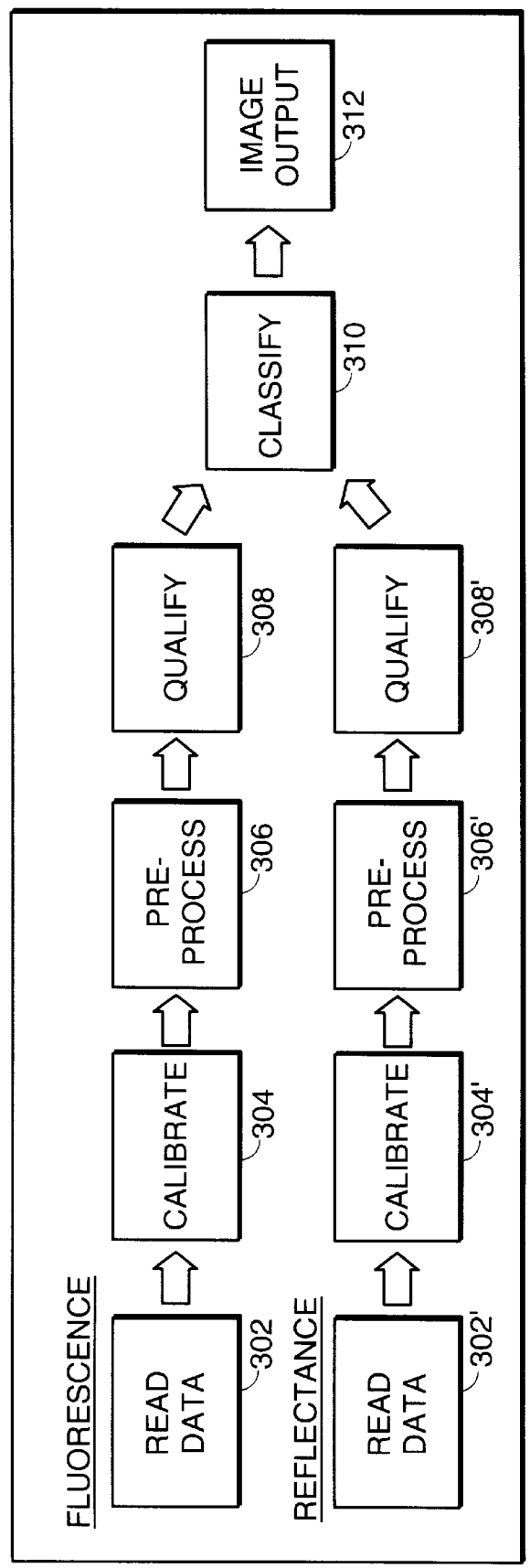
FIG. 3 is a schematic flow diagram of an illustrative spectral analysis process incorporating features of the invention.

FIG. 3 is a schematic flow diagram 300 of an illustrative spectral analysis process incorporating features of the invention. In FIG. 3, the flow of information for both the fluorescence spectra and the broadband reflectance spectra is explained in overview. FIG. 3 indicates that the computer 202 has processed one or more fluorescence spectra to the point where there is a suitable set of spectral results for analysis. With respect to fluorescence data, the illustrative analysis of FIG. 3 includes reading data 302, calibrating the data 304, pre-processing the data 306 and qualifying the data 308 as acceptable, valid data. With respect to the white light broadband reflectance spectra, the illustrative analysis of FIG. 3 includes reading the data 302', calibrating the data 304', pre-processing the data 306', and qualifying the data 308' as acceptable, valid data. The computer 202 combines the data obtained from the fluorescence spectra and the data obtained from the white light broadband reflectance spectra to classify (or characterize) the specimen in a classification step 310. As necessary, the spectroscopic system 100 generates an image from the two types of spectral data, and provides the image as output 312 in a form desired by the colposcopist/user, in either or both of a real-time video image or a recorded image in printed and/or electronic form.

Figure 4:
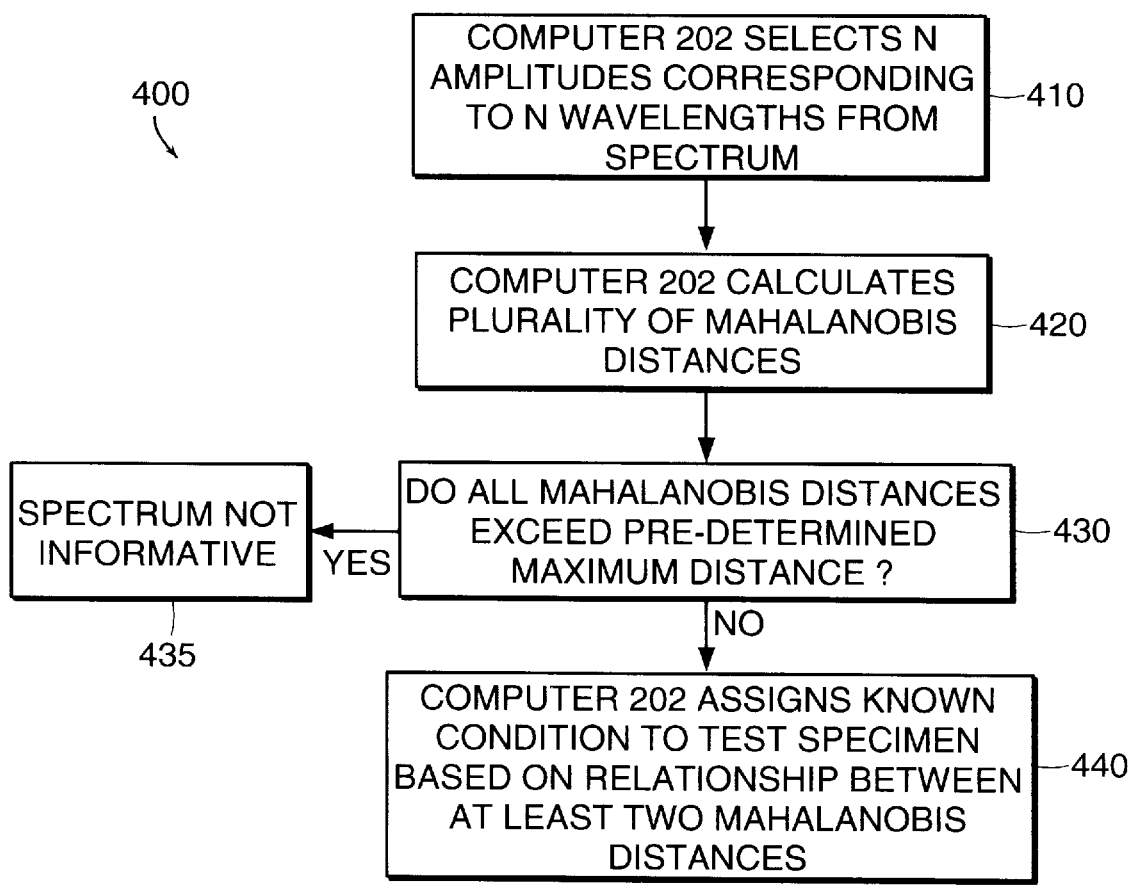
FIG. 4 is a more detailed schematic flow diagram depicting an exemplary classification step of the type depicted in FIG. 3 according to an illustrative embodiment of the invention.

FIG. 4 is a more detailed schematic flow diagram 400 depicting an exemplary classification step 310 of the type depicted in FIG. 3. In FIG. 4, as indicated in step 410, the computer 202 selects (N) quantitative features at (N) wavelengths from a spectrum which has been recorded from a test specimen. An exemplary method of selecting the (N) quantitative features is discussed in greater detail below with regard to FIG. 9. The illustrative embodiment describes the classification step in terms of Mahalanobis distances, but skilled artisans will appreciate that other metrics and other methods of comparing N-dimensional data may be used.

In some embodiments, the point in N-dimensional space characteristic of a specific constellation of reference data is a centroid of the N-dimensional points comprising the constellation of reference data. In another embodiment, the point in the N-dimensional space characteristic of a specific constellation of reference data is a weighted average of the N-dimensional points comprising the constellation of reference data, the weighting coming from an attribute of the spectrum from which the N-dimensional point in the constellation was taken. Those practiced in the spectroscopic arts understand that attributes such as signal-to-noise ratio, electronic baseline drift, or precision of calibrations are all reasons to place different confidence weightings on data. Another method for ascribing weighting factors is the use of analytical techniques such as regression analysis, in which the occurrence of a known condition is correlated with the presence of one or more independent variables. By way of example, if one can deduce, by application of regression analysis, that a known condition correlates to three independent variables with coefficients of 0.55 for the first, 0.65 for the second and 0.75 for the third, a weighting of 55% for the first variable, 65% for the second variable and 75% for the third variable (or their inverses) would be appropriate in computing the values of the coordinates of the characteristic point in N-dimensional space.

The metric between the N-dimensional point obtained from the test specimen and one of the plurality of reference constellations can be a distance from the point obtained from the test specimen to each of the representative points in the separate constellations. Likewise, the metric can be the result of measuring the distances from the N-dimensional point obtained from the test specimen to at least two of the N-dimensional points in a constellation and forming the average of the distances. The average can be a weighted average.

The metric between the N-dimensional point obtained from the test specimen and one of the plurality of reference constellations can be a probability or measure of association between the point obtained from the test specimen and the reference constellation.

Quantitative features in an optical spectrum are measurable attributes of that spectrum, or calculations based on them. Optical intensities at specific wavelengths in the spectrum represent one class of quantitative features that can be extracted from a spectrum. Other quantitative features, however, include the slopes of the spectrum at specific wavelength locations. One method for measuring the slope of a spectrum is based on the mathematics of discrete variables. In one embodiment, a slope can be computed as "the rise over the run," by observing a first intensity at a first wavelength and a second intensity at a second wavelength, and computing the difference between the two recorded intensities divided by the difference between the two wavelengths. This method of measuring a slope provides an average slope over an interval, which can be used in some embodiments to obtain a quantitative feature of a spectrum in an interval of wavelengths. In geometrical terms, such a slope is obtained as the straight line chord connecting the first intensity at the first wavelength with the second intensity at the second wavelength. Another method of obtaining a slope is based on mathematical principles of the calculus, in which the slope is taken to be the rate of change of an intensity or amplitude measured at a specific wavelength, or as is well understood by those of ordinary skill in calculus, the instantaneous rate of change of the intensity or of the amplitude, or the first derivative of the intensity. In some embodiments, an instantaneous slope at a selected wavelength can be employed as a quantitative feature of a spectrum. In geometrical terms, such a slope is obtained as the straight line tangent to the spectrum at the specific wavelength. As is well understood by those of ordinary skill in mathematics, higher order derivatives can also be used to describe spectra, and such higher order derivatives, as well as combinations of derivatives of different order, can be used as quantitative features of spectra.

Quantitative features can also be numbers extracted from the spectrum through integration of the spectrum over specific spectral regions. Quantitative features can be represented by numbers extracted from a spectrum by one method or by any combinations of methods.

In step 420, the computer 202 calculates a plurality of Mahalanobis distances. Each Mahalanobis distance is computed as a distance between the N-dimensional point corresponding to the (N) quantitative features of the test optical spectrum, and an N-dimensional point characteristic of a constellation, or group, of reference data. The reference data are a plurality of points in N-dimensional space, each such point corresponding to (N) quantitative features selected from a reference spectrum taken from a specimen having a known condition. The reference spectrum quantitative features are determined at the same wavelengths as those used for determining quantitative features of the test spectrum. The characteristic point is determined by aggregating the amplitudes of the reference data. In a preferred embodiment, the characteristic point is the centroid of the data. The N-dimensional coordinates of a centroid are determined by taking the average values of each of the quantitative features of the reference data. Mathematically, the ($i^{th}$) coordinate of the centroid is the arithmetic mean, or numerical average, of the ($i^{th}$) quantitative features of the plurality of reference data representing the known condition. This centroid is considered in this embodiment to be the type of a representative point of the constellation for the condition of the specimens represented by that constellation. Other kinds of aggregation can also be used. For example, taking the geometric mean, or the ($p^{th}$) root of the product of p quantitative features, where (p) is the number of reference spectra in the constellation. Still other aggregations can be used, such as computing the distances from the N-dimensional point representing the test specimen to all points in the reference constellation and then computing the average of these distances.

As indicated in step 430, the computer 202 computes a plurality of Mahalanobis distances, one to each characteristic point in each constellation from the N-dimensional point representing the test specimen. A detailed discussion of the Mahalanobis distance and methods used to calculate the Mahalanobis distance are presented below. The computer 202 then compares these Mahalanobis distances to a maximum value. If the computer 202 finds that no Mahalanobis distance is less than or equal to the maximum value, the computer 202 determines that the spectrum is uninformative, as step 435 indicates. If all Mahalanobis distances are greater than a maximum value, one can conclude that the test spectrum is sufficiently different from what might be expected that it is likely to be indicative of an unknown condition, or likely to contain erroneous information.

In step 440, the computer 202 assigns a known condition corresponding to a constellation of reference data to the test specimen, based in whole or in part on a relationship between at least two Mahalanobis distances. In a preferred embodiment, the determinative relationship is the shortest Mahalanobis distance.

Figure 5:
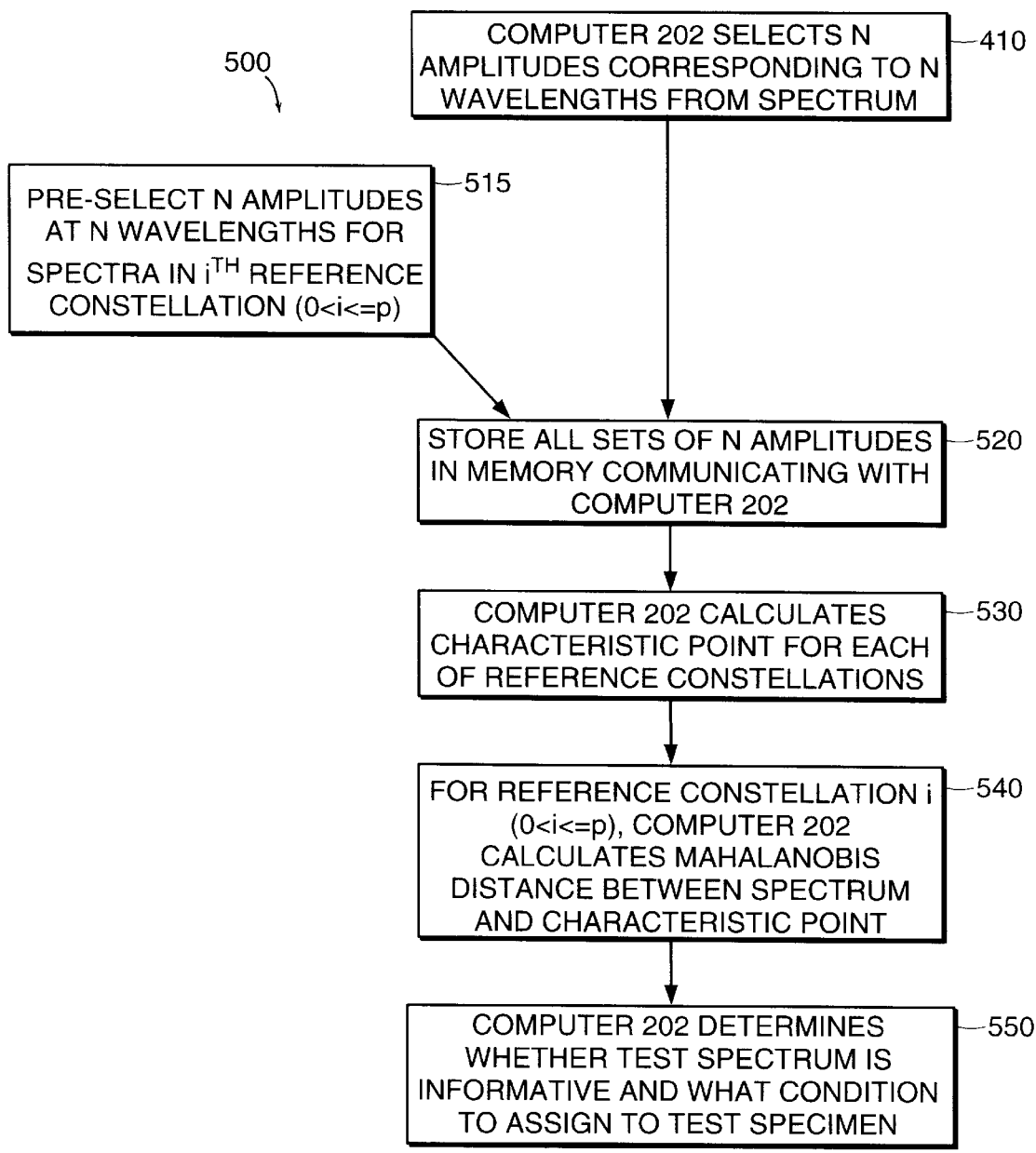
FIG. 5 is a detailed flow diagram showing the steps of an exemplary classification method corresponding to the classification step of FIG. 4, according to an illustrative embodiment of the invention.

FIG. 5 is a detailed flow diagram 500 showing the steps of an exemplary classification method corresponding to the classification step of FIG. 4. Beginning at step 410, the computer 202 selects (N) quantitative features corresponding to (N) wavelengths from a spectrum recorded from a specimen that is being tested. At step 515, which occurs preferably before the recording of a spectrum from a test specimen, the computer 202, or an equivalent computer, selects (N) quantitative features at (N) wavelengths of a spectrum recorded in an $i^{th}$ reference constellation, where i is greater than zero and less than or equal to a number p. In other embodiments, step 515 can also be contemporaneously performed with, or can even be performed after, step 410. In step 520, the computer 202 stores in a memory communicating with the computer 202 the various sets of (n) amplitudes. The memory can be a semiconductor memory, a magnetic or an optical memory or the like of a kind that allows the computer 202 to recover any amplitude value as it is needed for further calculation and analysis. In step 530, the computer 202 calculates a characteristic point using at least some of the (N) quantitative features that have been selected from each spectrum in a constellation of reference spectra. In one embodiment, the characteristic point is the centroid of the constellation of reference spectra. As mentioned earlier, in alternative embodiments other methods of computing a characteristic point can be used. In step 540, the computer 202 calculates a distance between the N-dimensional point representing the test spectrum in N-dimensional space, and the characteristic point for a constellation of reference spectra. The computer 202 performs this distance calculation for each of the constellations of reference spectra that are to be compared to the test spectrum. In one embodiment, the distance is a Mahalanobis distance.

Figure 11:
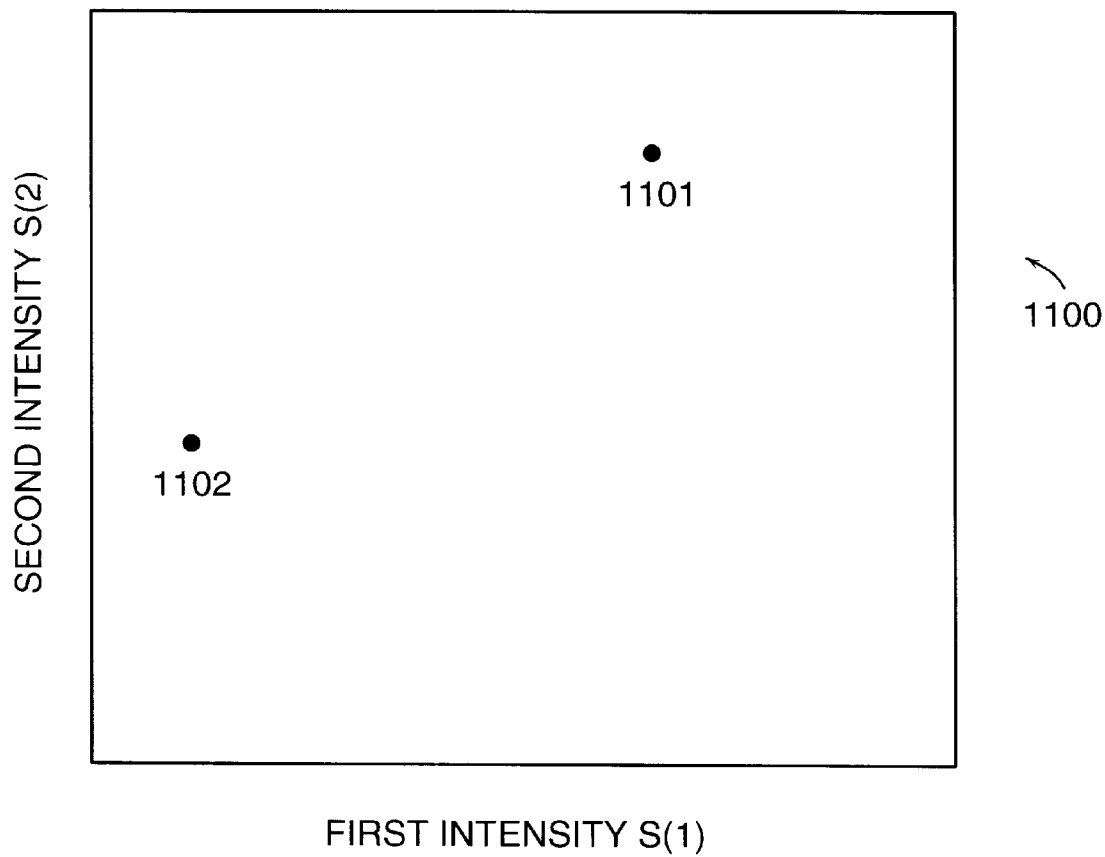
FIG. 11 is a graph depicting an exemplary plotting of two N-dimensional data points, where N=2, for the spectra shown in FIG. 10, according to an illustrative embodiment of the invention.
Figure 12:
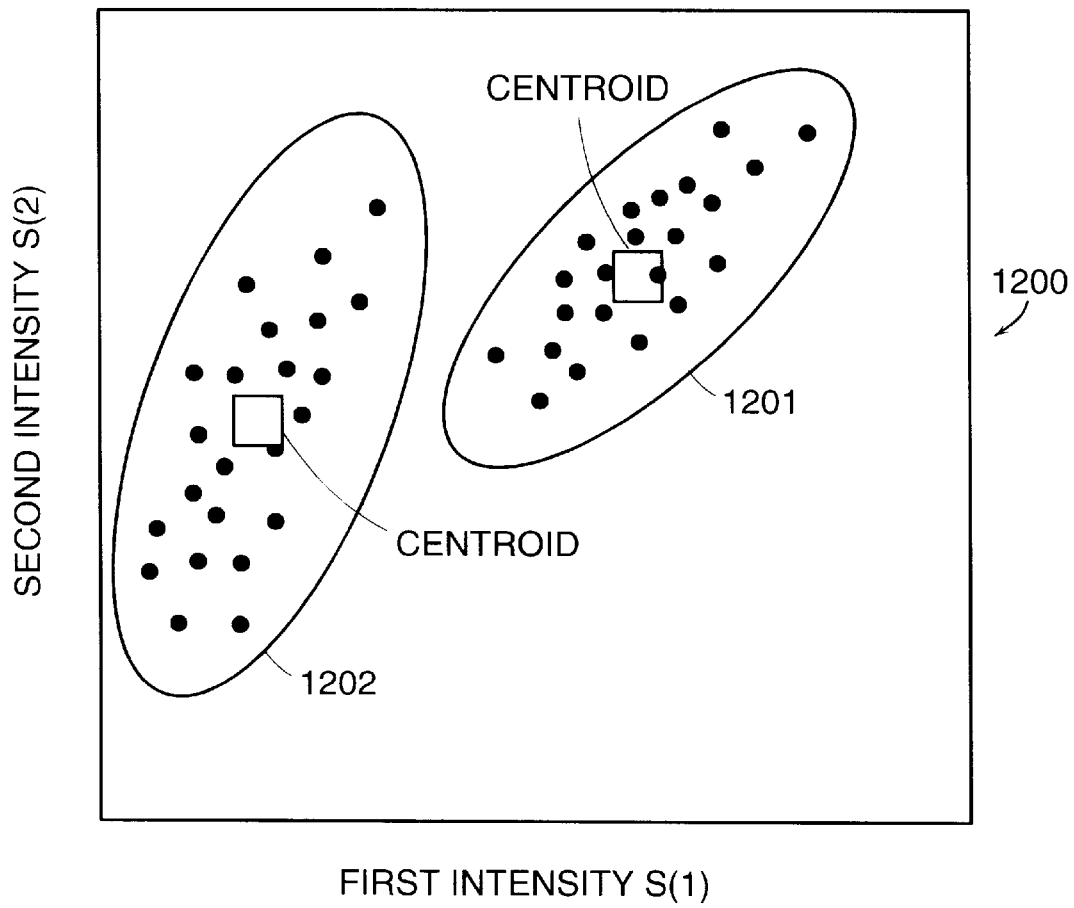
FIG. 12 is a graph depicting an exemplary plotting of many N-dimensional data points for two sets of reference spectra, where N=2, according to an illustrative embodiment of the invention.

Briefly, the Mahalanobis distance calculation is a weighted method of computing the distances from a point representing an unknown spectrum to the centroids of the constellations corresponding to spectra from specimens having known conditions. The weighting accounts for the fact that the neighborhood regions of the constellations are not circular regions in two-dimensional space, or hyperspherical regions in a multi-dimensional space. FIGS. 11 and 12 attempt to communicate that the regions are often elliptical, with major and minor axes.

A hypothetical example may be useful in explaining why a constellation can be expected to take on an elliptical shape in two dimensions, a shape resembling a prolate spheroid in three dimensions, and a hyper-prolate spheroid in multi-dimensional space. In principle, multiple spectra taken from specimens that have the same condition should be identical. However, given the realities of instrumental artifacts, slight differences in specimens, variations in technique and the like, it is not uncommon that one spectrum has slight differences from another, even if taken on the same instrument from the same specimen. In this example, the quantitative features extracted from the spectra are optical amplitudes at specific wavelengths. Next, suppose that the two spectra differ only by a scale factor, or multiplicative constant. The N-dimensional point corresponding to one would be plotted in N-dimensional space at a location defined by the coordinates $(x_1, x_2, x_3, \ldots, x_N)$, corresponding to the series of amplitudes selected from the spectrum. Suppose that the next spectrum were larger in amplitude by a factor of 1.5. The N-dimensional point corresponding to the next spectrum would then be given by the coordinates $1.5 *(x_1, x_2, x_3, \ldots, x_N)$, because each amplitude would be 1.5 times as large as the corresponding amplitude of the previous spectrum. These two points may be seen to lie along the same line in N-dimensional space connecting the origin and the point $(x_1, x_2, x_3, \ldots, x_N)$, with the second point lying at a greater distance from the origin than the first. In an idealized situation where there are many points corresponding to spectra taken from similar specimens, with the spectra differing only by a multiplicative constant, all the corresponding points lie along this same line. However, given the general observation that two spectra differ slightly in details beyond merely a multiplicative constant, the data points will lie somewhat off the hypothetical line connecting one or more points with the origin. Nevertheless, as long as the general shapes of the spectra do not differ strongly from one sample to another, any one point will not lie very far away from the line, and the constellation will tend to have an elongated axis in the direction of a characteristic line emanating from the origin.

The calculation of a Mahalanobis distance in (N) dimensions, where (N) is 2 or greater, is described below in terms of one illustrative embodiment. The illustrative embodiment is presented in reference to fluorescence spectra from cervical tissue. The fluorescence spectra are used in the determination of a state of health of the cervical tissue. As will be apparent to those of skill in the spectroscopic arts, other spectra taken using the same or other illumination, from the same or other kinds of specimens, may be analyzed using similar systems and methods.

Fluorescence from cervical tissue occurs over a limited spectral bandwidth. In one embodiment, excitation of 355 nm is employed, selected for its high output energy in the UV portion of the spectrum. The emission bandwidth of cervical tissue extends from about 375 nm to about 650 nm. The spectral region of interest for fluorescence spectra, $W_f=[375,650]$ nm, determines the range of wavelengths to be analyzed. The quantitative features taken from the set of wavelengths in the fluorescence spectrum can be specific amplitudes or optical intensities at selected wavelengths. Additionally, the quantitative features can be slopes of the spectral profile at selected wavelengths, or they could be any combination of amplitudes and slopes from the spectrum. Slopes are generated from the spectra in the computer 202 by computing a difference between the amplitude of the spectrum at a first wavelength and the amplitude of the spectrum at a second wavelength in proximity to the first wavelength, this difference being a measure of the slope at said first wavelength, which may also be divided by the difference in the two said wavelengths, for purposes of normalization.

In another method of extracting a quantitative feature from a spectrum, the amplitudes at wavelengths in the immediate vicinity of a first wavelength are averaged in the computer 202 to create a new amplitude at said first wavelength. The process is repeated at other wavelengths throughout the wavelength range of the spectrum. The number of wavelengths in the various vicinities of the representative wavelengths need not be the same as the number of wavelengths selected in the vicinity of the first wavelength. This process can be used to create one or a plurality of quantitative features from the spectrum that can be used alone or in combination with other quantitative features discussed herein.

According to the illustrative embodiment of the invention, a single spectrum recorded for a particular specimen is denoted as a series of quantitative features, one quantitative feature measured at each of a number p (where p>=N) of selected wavelengths. To simplify the discussion, it is assumed that amplitudes only are taken as the quantitative features from the spectra, but those practicing the art recognize that extension of this discussion to other quantitative features or combinations of quantitative features is possible. In equivalent mathematical terms, the $j^{th}$ spectrum is represented as the p-dimensional vector $S_j=(S_j(\lambda_1), S_j(\lambda_2), \ldots, S_j(\lambda_p))$ where $S_j(\lambda_k)$ represents the intensity of the $j^{th}$ spectrum at the $k^{th}$ wavelength $\lambda=\lambda_k$. In one embodiment, spectra from cervical tissue specimens that exhibit normal health, metaplasia, CIN I, and CIN II/III are designated by the symbols N, M, L, and H, respectively. For example, the value of the intensity of the $j^{th}$ normal health sample at the $k^{th}$ wavelength is denoted by $N_{jk}=N_j(\lambda_k)$, with similar definitions for $M_{jk}$, $L_{jk}$, and $H_{jk}$. In other embodiments, specimens that exhibit more than four states of health, or fewer than four states of health may be analyzed. In still other embodiments, the conditions that are being analyzed are plural numbers of conditions that can be investigated spectroscopically other than states of health, and the test and reference specimens are substances other than cervical tissue.

In one embodiment, the computer 202 assigns variables expressed in mathematical terms as $n_1$, $n_2$, $n_3$, and $n_4$ to be the number of reference spectra representing specimens exhibiting normal health, CIN II/III, metaplasia, and CIN I spectra, respectively, and $$n = \sum_{j=1}^{4} n_j.$$

In one embodiment, the $n_1 \times p$ matrix N of reference data obtained from spectra recorded from specimens that exhibit normal health is denoted by equation (1).

$$N = \begin{bmatrix} N_{11} & N_{12} & \cdots & N_{1p} \\ N_{21} & N_{22} & \cdots & N_{2p} \\ \vdots & \vdots & \cdots & \vdots \\ N_{n_1 1} & N_{n_1 2} & \cdots & N_{n_1 p} \end{bmatrix} \quad (1)$$

Each row of matrix N represents the p amplitudes measured for a spectrum taken from a reference specimen that exhibits normal health. There are $n_1$ such spectra, and $n_1$ such rows. Similar definitions apply to the matrices H, M. and L of reference data for specimens that exhibit CIN II/III, metaplasia, and CIN I, respectively. The nxp matrix $$X = \begin{bmatrix} N \\ H \\ M \\ L \end{bmatrix}$$

is called the data matrix, and is generated by concatenating the N, H, M and L matrices, all of which have rows of p entries each.

In one embodiment, for example the case in which the computer 202 compares two conditions, for example, normal health data and CIN II/III data, the data matrix becomes $$X = \begin{bmatrix} N \\ H \end{bmatrix}.$$

Let $T_1=N$, $T_2=H$, $T_3=M$, and $T_4=L$ designate the data matrices for the $j^{th}$-tissue classes. In one embodiment, tissue class 1 comprises specimens exhibiting normal health, tissue class 2 comprises specimens exhibiting CIN II/III, tissue class 3 comprises specimens exhibiting metaplasia, and tissue class 4 comprises specimens exhibiting CIN I.

The computer 202 defines the pxp group covariance matrix $\Sigma_j$ associated with the $j^{th}$ tissue class by the relation $$\Sigma_j = \mathrm{cov}(T_j) = \frac{1}{n_j - 1}(T_j - \langle T_j \rangle)^T (T_j - \langle T_j \rangle).$$

The computer 202 defines the $n_j$xp-matrix of column averages $<T_j>$ (i.e., the group mean matrix for tissue class j) by the relation $$\langle T_j \rangle = \begin{bmatrix} \overline{T}_j(1) & \overline{T}_j(2) & \cdots & \overline{T}_j(p) \\ \overline{T}_j(1) & \overline{T}_j(2) & \cdots & \overline{T}_j(p) \\ \vdots & \vdots & \cdots & \vdots \\ \overline{T}_j(1) & \overline{T}_j(2) & \cdots & \overline{T}_j(p) \end{bmatrix}.$$

The computer 202 defines the column-wise average $\overline{T}_j(k)$ of the $k^{th}$-wavelength over the $n_j$ spectra from tissue class j by the relation $$\overline{T}_j(k) = \frac{1}{n_j} \sum_{i=1}^{n_j} T_j(i, k).$$

The computer 202 calculates the pooled within-group covariance matrix $\Sigma$ as the weighted average of the group covariance matrices, which matrix $\Sigma$ is expressed as $$\Sigma = \frac{1}{n-4} \sum_{j=1}^{4} (n_j - 1) \cdot \Sigma_j \quad (2)$$

The computer 202 computes the group mean as the vector whose components comprise the column averages of the $j^{th}$-data matrix: $\overline{T}_j=(\overline{T}_j(1), \overline{T}_j(2), \ldots, \overline{T}_j(p))$. The Mahalanobis distance from an unclassified test spectrum $S=(S(\lambda_1), S(\lambda_2), \ldots, S(\lambda_p))$ obtained from a test specimen to a group mean is defined using equation (3).

$$d(S, T_j) = \sqrt{\left|(S - T_j) \cdot \Sigma^{-1} \cdot (S - T_j)^T\right|} \quad (3)$$

In one embodiment, for example, $\min_{1 \leq j \leq 4} d(S, \overline{T_j})$ is achieved for $j=3$, then the spectrum S is classified as a class 3 spectrum, and the specimen from which the spectrum was recorded is assigned the condition of class 3, namely metaplasia tissue.

In one embodiment, the metric can be a distance measured from the N-dimensional point representing the test specimen to the centroid of each constellation, said distance computed in one of a number of ways. In one method of calculation, the distance is the square root of the sum of the squares of the differences in coordinates of points in the N-dimensional space. In another calculation, the distance is the Mahalanobis distance. In yet another calculation, the distance is the Bhattacharyya distance.

For two groups, $g_1$ and $g_2$, the Bhattacharyya distance is written as $$d^2(g_1, g_2) = \frac{1}{8}(\vec{\mu}_2 - \vec{\mu}_1)\left(\frac{1}{2}(C_1 + C_2)\right)^{-1}(\vec{\mu}_2 - \vec{\mu}_1)^T + \frac{1}{2}\ln\left|\frac{\det\left(\frac{1}{2}(C_1 + C_2)\right)}{\sqrt{\det(C_1)\det(C_2)}}\right|$$

Vectors $\mu_1$ and $\mu_2$ are the mean vectors for each group, $C_1$ and $C_2$ are the covariance matrices for the groups, and the values for the determinants of these matrices are indicated by $\det(.)$. The above equation is used to determine the distance between two groups, which can be two constellations of data points in N-dimensional space representing two kinds of reference specimens that exhibit known conditions. As an example, the reference specimens can be two tissue specimens that exhibit known states of health, and the groups can be reference data in N-dimensional space that are representative of the known conditions. If the Mahalanobis distance (the distance from a single point representing a specimen of unknown condition to a group) is greater than a multiplicative factor (for example, a factor of 5) of the Bhattacharyya distance, then the spectrum identified by the point representing the specimen of unknown condition does not belong to either group, and the specimen is not to be described by either condition, or classification.

One important aspect of the previous analysis is the idea of normalization, which is the subject of a co-pending application, entitled "System for Normalizing Spectra" and identified by Attorney Docket Number MDS-020, filed on even date herewith. There are many possible normalization schemes. Among the approaches described in the co-pending application identified by Attorney Docket Number MDS-020 is non-uniform segment normalization. According to one embodiment, in non-uniform segment normalization, a given spectrum $S=(S(\lambda_1), S(\lambda_2), \ldots, S(\lambda_p))$ is normalized by $$A_S = \sum_{j=1}^{r-1} S(\lambda_j)|\lambda_{j+1} - \lambda_j|$$

which is the approximate area under selected segments of the spectrum that include a subset of the wavelengths in the range $((\lambda_1),(\lambda_2), \ldots,(\lambda_p))$. The selected segments can be disjoint. The normalized spectrum is denoted as:

$$S_A = \frac{1}{A_S}S.$$

Other normalization approaches are also discussed in Attorney Docket Number MDS-020.

The spectra are such that the covariance matrix $\Sigma$, from equation (2), can be singular. Thus, the number of wavelengths analyzed must be reduced to the rank of $\Sigma$ (or less). This is achieved via the Mahalanobis distance as given in equation (3). Divide the wavelength region $I=[\lambda_o, \lambda_f]$ into smaller sub-regions $I_j=[\lambda_{oj}, \lambda_{fj}]$ and sample each sub-region in bins of length 10 nm. That is, let $\text{bin}_j(k)=[\lambda_{ok}+10 \cdot (k-1), \lambda_{ok}+10 \cdot k]$ for $$k = 1, 2, \ldots, \left\lfloor \frac{\lambda_{fj} - \lambda_{oj}}{10} \right\rfloor$$

where $[\cdot]$ is the least integer function. Each normalized spectrum $S_A$ is reduced to the average of the normalized data over the bins. Two bins are used over each spectrum so that the reduced spectrum has the form $$S_R(j, k) = \left(\frac{1}{|\text{bin}_1(j)|} \cdot \sum_{\lambda \in \text{bin}_1(j)} S_A(\lambda) \cdot 1_j, \frac{1}{|\text{bin}_2(k)|} \cdot \sum_{\lambda \in \text{bin}_2(k)} S_A(\lambda) \cdot 1_k\right)$$

where $1_j$ and $1_k$ are vectors each of whose components is 1 and whose lengths are $|\text{bin}_1(j)|$ and $|\text{bin}_2(k)|$, respectively. The reduced covariance matrix $\Sigma_{jk}$ is computed as the weighted sum of the reduced group covariance matrices, $\Sigma_i(j,k)$. The $\Sigma_i(j,k)$ in turns are computed from the reduced spectra in each tissue class as is the reduced data matrix $X_{jk}$. If $X_{jk}(a)$ is the $a^{th}$-row of the reduced data matrix $X_{jk}$, then the Mahalanobis distance from the $a^{th}$-row to the $b^{th}$-row is given by (4).

$$d(a, b) = \sqrt{\left|(X_{jk}(a) - X_{jk}(b)) \cdot \Sigma_{jk}^{-1} \cdot (X_{jk}(a) - X_{jk}(b))^T\right|} \quad (4)$$

Continuing with FIG. 5, in step 550, the computer 202 compares the different distances calculated in step 540, and determines whether the test spectrum is informative. The test spectrum is informative if at least one distance is shorter than a pre-defined maximum value. In such an embodiment, the distance can be understood to represent a dissimilarity between a test spectrum and a constellation of reference spectra as represented by a characteristic point. The larger the distance, the greater the dissimilarity between the test spectrum and the constellation of reference spectra. One cannot reasonably deduce anything definitive about a test spectrum that is very dissimilar from a reference spectrum or constellation of reference spectra, other than that the test spectrum is not likely to be indicative of a condition represented by the specimens that were examined to obtain the reference spectra. If the dissimilarity to every reference constellation is too large, the test spectrum is not likely to represent a condition identifiable with any constellation, and the test spectrum is deemed to be uninformative.

In addition, in step 550, if a test spectrum is deemed to be informative, the test specimen can be assigned a condition corresponding to a constellation of reference spectra. In one embodiment, the condition that is assigned is the condition of the constellation of reference spectra having the shortest distance from the point corresponding to the test spectrum. The constellation of reference spectra having the shortest distance from the point corresponding to the test spectrum can be understood to be the constellation most similar to the test spectrum. In other embodiments, other selection criteria that consider the relationship of the test spectrum to one or more constellations of reference spectra, can be used.

Figure 6:
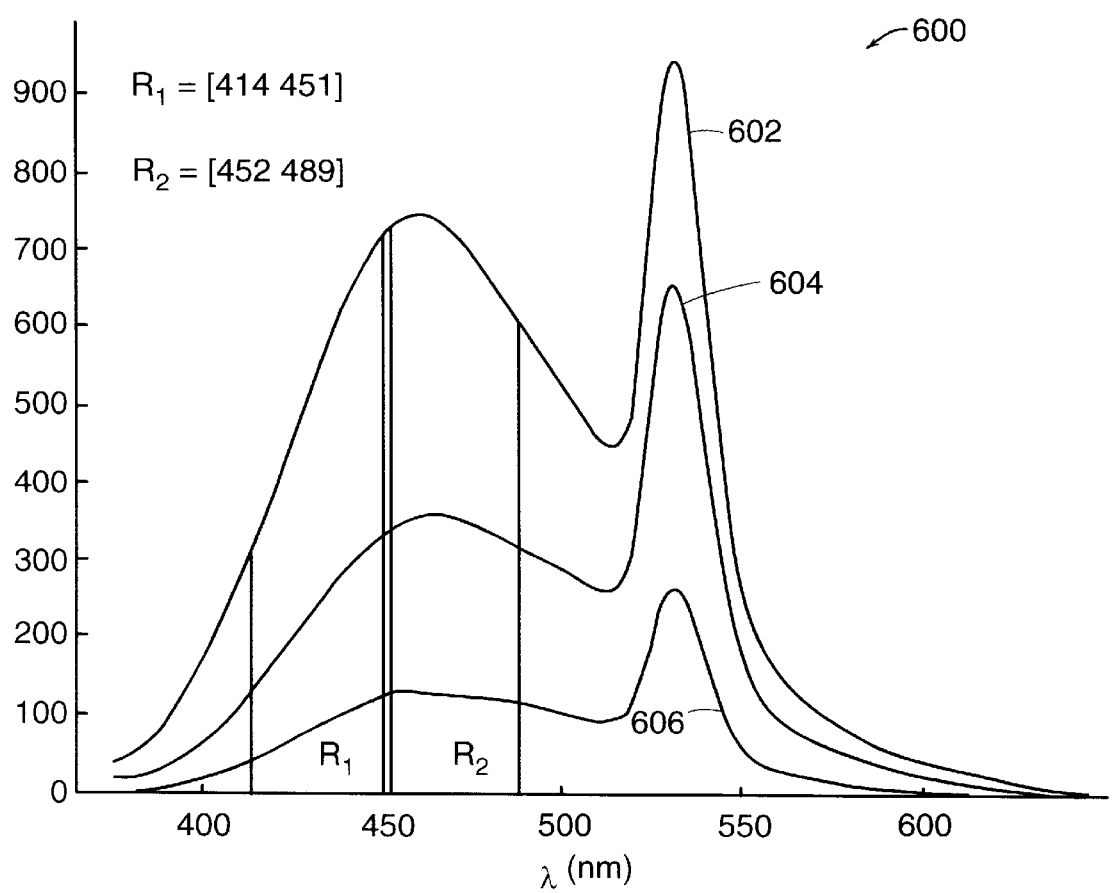
FIGS. 6–8 are graphs depicting a selection of particular wavelength regions for applying a characterization method according to illustrative embodiments of the invention.
Figure 7:
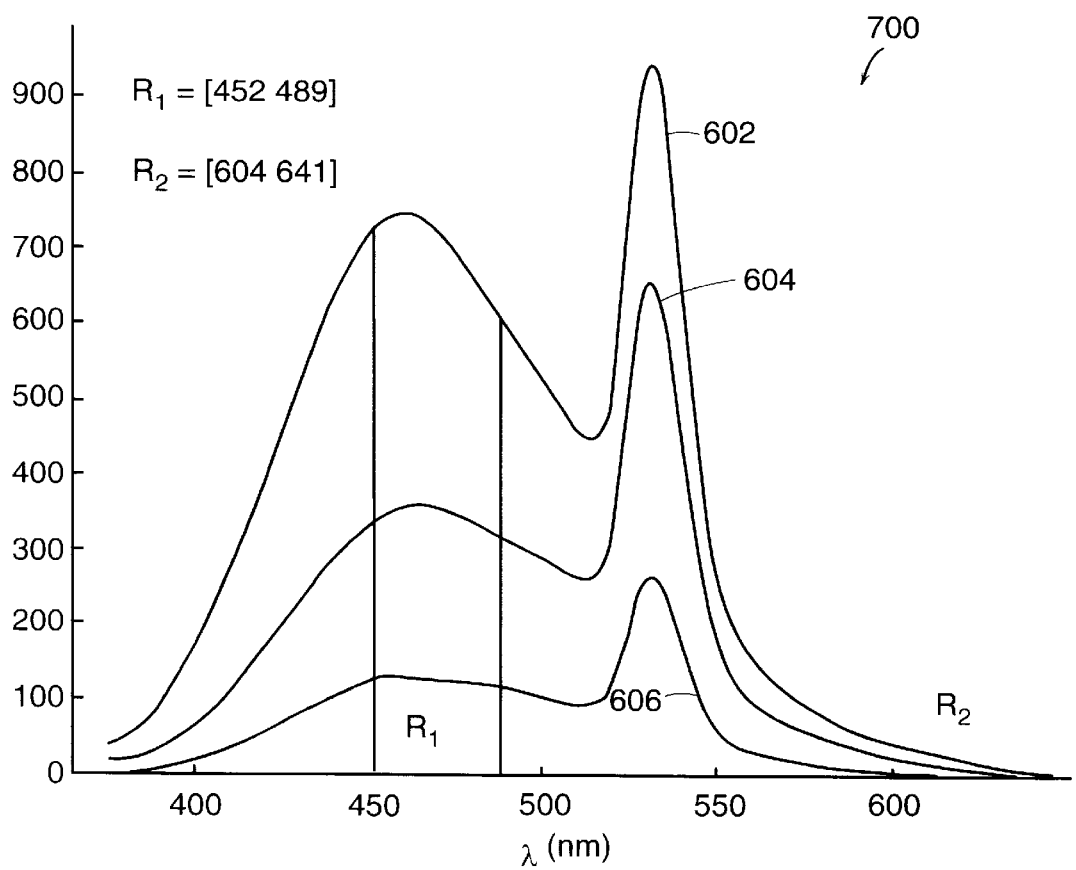
Figure 8:
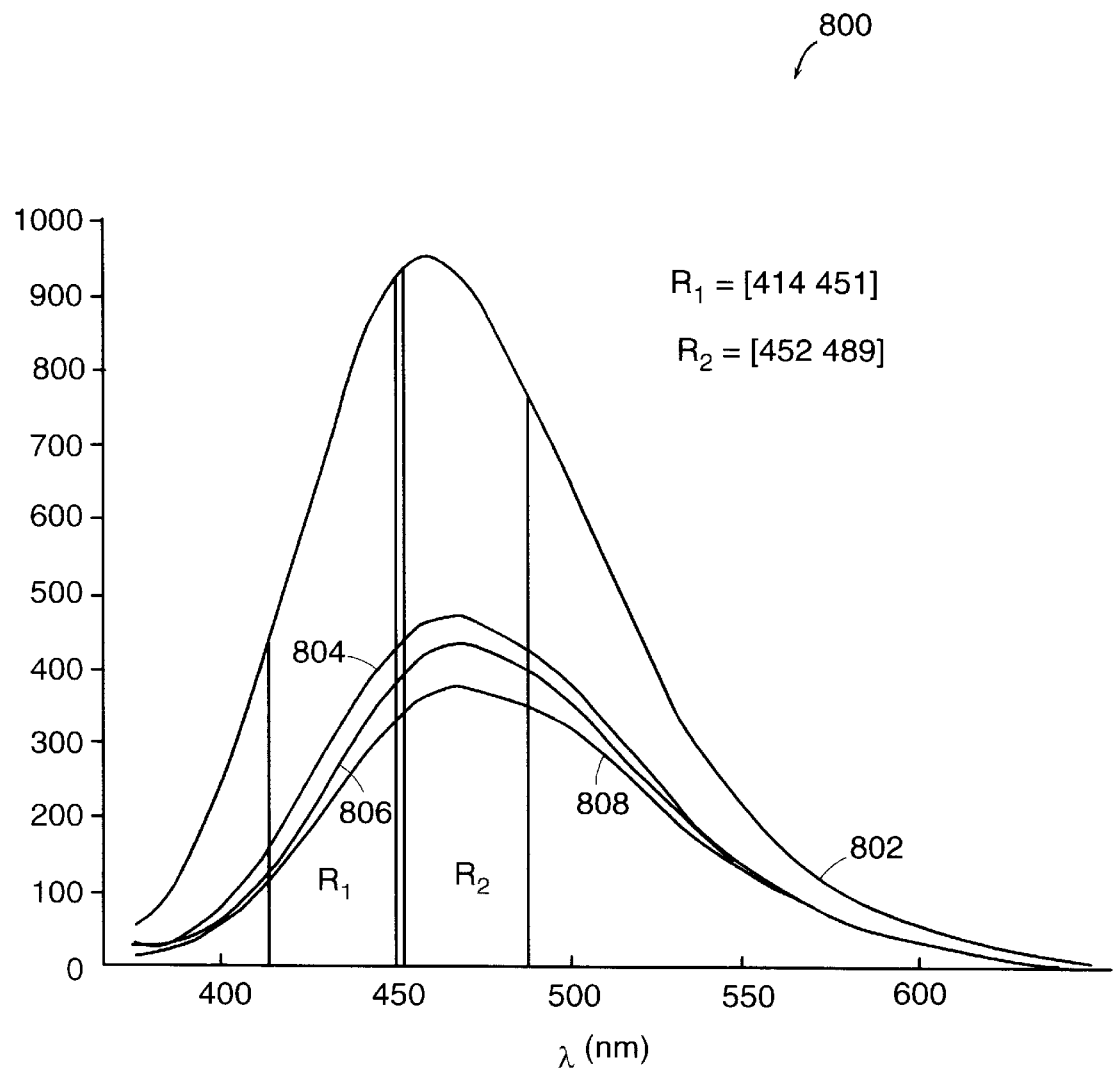

FIGS. 6–8 are graphs depicting a selection of particular wavelength regions for applying a characterization method. FIG. 6 is a graph 600 depicting a selection of particular wavelength regions in which amplitudes can be selected as a function of wavelength according to the invention. In one embodiment, the specimen is illuminated with ultraviolet radiation of a wavelength of 355 nm from a frequency-tripled Nd:YAG laser.

As depicted in FIG. 6, fluorescence spectra are recorded from various tissue specimens having different disease states, or different states of health. The spectrum 602 is typical of healthy cervical tissue comprising normal squamous cells. Cervical tissue can exhibit pre-cancerous lesions known as cervical intraepithelial neoplasia (CIN), a condition that has been divided into three grades. CIN I is the mildest form of the neoplasia, and most often regresses to normal tissue without intervention. CIN II and CIN III are more severe grades of the neoplasia, with CIN III being a potential signal for progression into carcinoma in-situ (CIS). Often, the course of treatments for CIN II and CIN III are similar, including removal of the tissue through biopsy or Loop Electro-Excision Procedure (LEEP), so pathologists usually combine the diagnosis of CIN II and CIN III together as CIN II/III. The spectrum 604 in FIG. 6 is typical of CIN II/III. The spectrum 606 is typical of CIN I.

In FIG. 6, two regions are indicated by vertical lines that intersect the three spectra 602, 604, 606. These vertical lines define two regions, one labeled R1, extending from the wavelengths 414 nm to 451 nm inclusive, and another labeled R2, extending from 452 nm to 489 nm inclusive. In one embodiment, amplitudes within these regions are selected. These spectral regions provide data that most readily distinguish the conditions of normal health and of CIN II/III.

According to an illustrative embodiment of the invention, the computer 202 selects and records a value, for example, a digitized value of the amplitude at a defined set of wavelengths within each region that has been selected. In the embodiment described in FIG. 6, the computer 202 can, for example, select and record one or more digitized amplitudes for region R1 and one or more digitized amplitudes for region R2.

Turning to FIG. 7, a graph 700 depicts the same three spectra 602, 604 and 606 that are shown in FIG. 6. The spectra 602, 604, 606 each have a 532 nm peak. In FIG. 7, the region R1 is selected by the computer 202 as the wavelength range 452 nm to 489 nm, and the region R2 is selected by the computer 202 as the wavelength range 604 nm to 641 nm. In another illustrative embodiment, the computer 202 can, for example, select and record one or more digitized amplitudes for region R1 and one or more digitized amplitudes for region R2, to distinguish between two conditions.

In FIG. 8, a graph 800 shows four spectra 802, 804, 806 and 808, which do not include the "green spike" feature at 532 nm that appears in the spectra shown in FIGS. 6 and 7. In FIG. 8, a region denoted R1 is selected by the computer 202 as the wavelength range 414 nm to 451 nm, and the region denoted R2 is selected by the computer 202 as the wavelength range 452 nm to 489 nm. In yet another illustrative embodiment, the computer 202 can, for example, select and record one or more digitized amplitudes for region R1 and one or more digitized amplitudes for region R2, to distinguish between two conditions. As will be apparent to those of skill in the spectroscopic arts, many different types of spectra can be recorded, depending on such parameters as the condition of a specimen, the type of illumination that is employed, and the range of wavelengths that are examined. While the illustrative embodiments shown in FIGS. 6–8 show the selection of two regions R1 and R2, it will be recognized by those of ordinary skill in the spectroscopic arts that a plurality of regions can be selected, the plurality including more than two regions.

Figure 9:
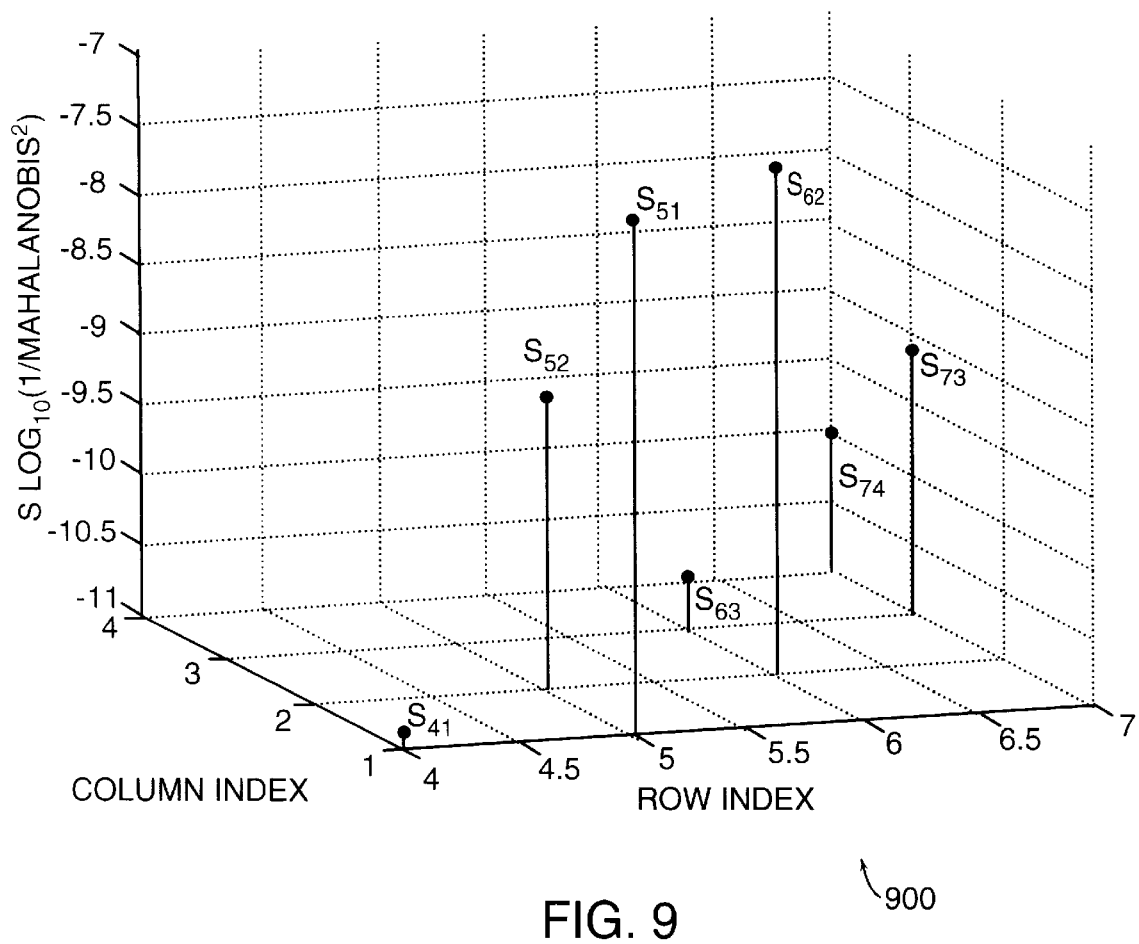
FIG. 9 is a graph depicting an exemplary analysis for finding the appropriate data for plotting in an N-dimensional plot, according to an illustrative embodiment of the invention.

FIG. 9 is a graph 900 depicting an exemplary analysis for finding the appropriate data for plotting in an N-dimensional plot. The vertical axis of FIG. 9 is a quantity that depends on the inverse of the square of a Mahalanobis distance. The two horizontal axes represent values of row indices and of column indices in a reduced group mean data matrix $X_{jk}$, described in more detail below, that is designed to enable the computer 202 to select spectral regions that optimize the ability to discriminate between two spectral types. The points plotted in FIG. 9 indicate the magnitude of the sum $s_{jk}$ described below at a specific row and column of the $X_{jk}$ matrix.

As described above, the wavelengths under consideration in the analysis of the sprectra of interest do not necessarily include all of the wavelengths in the entire spectrum. The computer 202 divides the spectral regions of interest into segments, or "bins," of defined, preferably equal, numbers of amplitudes.

In one embodiment, the computer 202 divides a spectral region into a range of wavelengths, $W_j=[\lambda_{0j}, \lambda_{f1}]$ for $j=1,2$ where $\lambda_{0j}$ is the shortest wavelength in the $j^{th}$ range and $\lambda_{f1}$ is the longest wavelength in the $j^{th}$ range, and $$\text{bin}_j\{k\}=[\lambda_{oj}+10*(k-1), \lambda_{oj}+10*k] \qquad (6)$$

for $k=1, 2, \ldots, m_j$, $$m_j = \left\lfloor \frac{\lambda_{fj} - \lambda_{0j}}{10} \right\rfloor,$$

$j=1,2$ where $\lfloor \cdot \rfloor$ is the least integer function (i.e., $\lfloor \bullet \rfloor$=floor $(x)$). For each wavelength bin pairing $(\text{bin}_1(j), \text{bin}_2(k))$ and each (normalized) spectrum, the computer 202 computes the 2-dimensional points $$P_N(n)_{j,k} = \left( \sum_{\lambda \in bin_1\{j\}} N_A(n,\lambda)|\Delta\lambda|, \sum_{\lambda \in bin_2\{k\}} N_A(n,\lambda)|\Delta\lambda| \right) \qquad (7)$$

for $n=1, 2, \ldots, n_1$ and $$P_H(h)_{j,k} = \left( \sum_{\lambda \in bin_1\{j\}} H_A(h,\lambda)|\Delta\lambda|, \sum_{\lambda \in bin_2\{k\}} H_A(h,\lambda)|\Delta\lambda| \right) \qquad (8)$$

for $h=1, 2, \ldots, n_4$.

As defined above, $n_1$ is the number of reference specimens exhibiting normal health samples, and $n_4$ is the number of CIN I/I samples. $N_A$, $H_A$ represent normalized reference spectra corresponding to normal health and CIN II/III, respectively. The computer 202 can select the m-dimensional vector that contains the $l^{th}$ sample of the normalized normal health data at wavelengths $\lambda_1, \lambda_2, \ldots,$ $\lambda_m$ which is designated as $N_A(l)=(N_A(l,\lambda_1),N_A(l,\lambda_2), \ldots, N_A(l,\lambda_m))$. The computer 202 can construct the vector $N_A(l)_{j,k}$ to be the sub-vector of $N_A(l)$, whose wavelengths are sampled at $\{\lambda_{j1},\lambda_{j2}, \ldots ,\lambda_{j,m_{1j}}\} \in bin_1\{j\}$ and $\{\lambda_{k1}, \lambda_{k2}, \ldots ,\lambda_{k,m_{2k}}\} \in bin_2\{k\}$, where $m_{1j}$ is the number of wavelengths in $bin_1\{j\}$, $m_{2k}$ is the number of wavelengths in $bin_2\{k\}$, and $m_{1j}+M_{2k}<m$ (total number of wavelengths). In equivalent mathematical terms, $$N_A(l)_{j,k}=(N_A(l, \lambda_{j1}),N_A(l,\lambda_{j2}), \ldots ,N_A(l,\lambda_{j,m_{1j}}),N_A(l,\lambda_{k1}),N_A(l,\lambda_{k2}), \ldots ,N_A(l,\lambda_{k,m_{2k}})) \quad (9)$$

for $l=1, 2, \ldots, n_1$. The computer 202 can equally select and construct a similar vector for a spectrum corresponding to a reference specimen known to exhibit CIN II/III, namely $H_A(h)_{j,k}$, $h=1, 2, \ldots, n_4$.

The computer 202 can compute a reduced data matrix $X_{j,k}$ for the bin pair $(bin_1(j),bin_2(k))$ according to equation (10).

$$X_{j,k} = \begin{bmatrix} N_A(1)_{j,k} \\ N_A(2)_{j,k} \\ \vdots \\ N_A(n_1)_{j,k} \\ H_A(1)_{j,k} \\ H_A(2)_{j,k} \\ \vdots \\ H_A(n_4)_{j,k} \end{bmatrix}_{(n_1+n_4)\times(m_1+m_2)} \quad (10)$$

The computer 202 can construct vectors $1_{1j}=1,1, \ldots ,1)_{1\times m_{1j}}$ and $1_{2k}=(1,1, \ldots ,1)_{1\times m_{2k}}$ which are vectors comprising $m_{1j}$ elements and $m_{2k}$ elements, all of which are 1. The computer 202 can compute $P_N^*(n,1)_{j,k}$ and $P_N^*(n,2)_{j,k}$ to be the first and second coordinates of $P_N^*(n)_{j,k}$, weighted by their bin lengths, according to equations 11 and 12.

$$P_N^*(n, 1)_{j,k} = \frac{1}{|bin_1\{j\}|} \sum_{\lambda \in bin_1\{j\}} N_A(n, \lambda)|\Delta\lambda| \quad (11)$$

$$P_N^*(n, 2)_{j,k} = \frac{1}{|bin_2\{k\}|} \sum_{\lambda \in bin_2\{k\}} N_A(n, \lambda)|\Delta\lambda| \quad (12)$$

$n=1,2, \ldots, n_1$, $|bin_1 \{j\}|$ is the bin length of $bin_1\{j\}$ (i.e., the number of wavelengths in $bin_1\{j\}$).

The computer 202 can compute in a similar manner $P_H^*(n,1)_{j,k}$ and $P_H^*(n,2)_{j,k}$ for the spectra representing CIN II/III reference specimens.(see, equations (11) and (12) below The computer 202 can compute the reduced group mean matrix, $\overline{XX}_{jk}$ as defined by equation (13), $$\overline{XX}_{jk} = \begin{bmatrix} P_N^*(1, 1)_{jk} \cdot l_{1j} & P_N^*(1, 2)_{jk} \cdot l_{1k} \\ \vdots & \vdots \\ P_N^*(n_1, 1)_{jk} \cdot l_{1j} & P_N^*(n_1, 2)_{jk} \cdot l_{1k} \\ P_H^*(1, 1)_{jk} \cdot l_{1j} & P_H^*(1, 2)_{jk} \cdot l_{1k} \\ \vdots & \vdots \\ P_H^*(n_4, 1)_{jk} \cdot l_{1j} & P_H^*(n_4, 1)_{jk} \cdot l_{1k} \end{bmatrix}_{(n_1+n_4)\times(m_1+m_2)} \quad (13)$$

and the computer 202 can compute the reduced covariance matrix according to equation 14:

$$C_{jk} = \left[(X_{jk} - \overline{XX}_{jk})^T(X_{jk} - \overline{XX}_{jk}) \cdot \frac{1}{m_1+m_2-2}\right]_{(m_1+m_2)\times(m_1+m_2)} \quad (14)$$

The computer 202 can calculate reduced Mahalanobis matrix as $M_{jk}=C_{jk}^{-1}$ and the reduced Mahalanobis distance between rows in the reduced data matrix $X_{jk}$ is given by equation (15)

$$D(p, q)_{jk} = \sqrt{|(X(p)_{jk} - X(q)_{jk})M_{jk}(X(p)_{jk} - X(q)_{jk})^T|} \quad (15)$$

where $X(p)_{jk}$ is the $p^{th}$ row of $X_{jk}$.
For each bin pairing, $(bin_1(j),bin_2(k))$, the computer 202 computes the sum $S_{jk}$ as per equation (16).

$$S_{jk} = \sum_{t_1 \in bin_1\{j\}} \sum_{t_2 \in bin_2\{k\}} \frac{1}{D(t_1, t_2)_{jk}^2} \quad (16)$$

The set of wavelength indices $\{t_1, t_2\}$ which minimizes $S_{jk}$, is an optimized wavelength subset that the computer 202 can use to construct the Mahalanobis matrix.

In one embodiment, the results of such a computation have been determined. The sums and their numerical values are listed in Table 1.

| Bin pair (j,k) | Sum $S_{jk}$ |
| --- | --- |
| (4,1) | $0.00013460783366 * 10^{-7}$ |
| (5,1) | $0.45718183093151 * 10^{-7}$ |
| (5,2) | $0.01288741892447 * 10^{-7}$ |
| (6,2) | $0.37301027345268 * 10^{-7}$ |
| (6,3) | $0.00024434477467 * 10^{-7}$ |
| (7,3) | $0.00824980009694 * 10^{-7}$ |
| (7,4) | $0.00085705932298 * 10^{-7}$ |

Table 1. Mahalanobis Sums

The linearity of the bin pairings is represented as follows:
$P_N^*(n)_{51}=(P_N^*(m,1)_{51},P_N^*(n,2)_{51})$, $P_H^*(h)_{51}=(P_H^*(h,1)_{51},P_H^*(h,2)_{51})$, $P_N^*(n)_{62}=(P_N^*(m,1)_{62},P_N^*(n,2)_{62})$, $P_H^*(h)_{62}=(P_H^*(h,1)_{62},P_H^*(h,2)_{62})$, and $P_N^*(n)_{73}=(P_N^*(m,1)_{73},P_N^*(n,2)_{73})$, $P_H^*(h)_{73}=(P_H^*(h,1)_{73},P_H^*(h,2)_{73})$, for $n=1,2, \ldots ,n_1=26$ and $h=1,2, \ldots ,n_4=21$.
The bin pairing
$P_N^*(n)_{41}=(P_N^*(m,1)_{41},P_N^*(n,2)_{41})$, $P_H^*(h)_{41}=(P_H^*(h,1)_{41},P_H^*(h,2)_{41})$, has the smallest Mahalanobis sum $S_{41}=1.3*10^{-11}$.

The sum $s_{jk}$ measures the effectiveness of the Mahalanobis distances on tissue classification. That is if $d(a,b)$ is small, then $X_{jk}(a)$ is close to $X_{jk}(b)$ and hence.

$$\frac{1}{(d(a, b))^2}$$

is large. That is, the spectra represented by $X_{jk}(a)$ and $X_{jk}(b)$ are close, and the specimens from which the spectra were recorded belong to the same tissue class, or exhibit the same condition or state of health. If, conversely, $d(a,b)$ is large, then $X_{jk}(a)$ is "far away form" $X_{jk}(b)$ and hence $$\frac{1}{(d(a,b))^2}$$

is small. One may infer that the spectra represented by $X_{jk}(a)$ and $x_{jk}(b)$ are different, and the specimens from which they were recorded belong to distinct tissue classes, or exhibit different conditions. Thus, the computer 202 can determine the wavelengths that give the best separation between tissue classes by identifying a minimum sum $s_{jk}$.

In one embodiment, the computer 202 requires $s_{jk}<10^{-6}$, and determines the wavelength regions of interest in order to obtain maximal discrimination between spectra representing tissues that exhibit different states of health are [405,445] nm and [460,500] nm. The computer 202 uses a first wavelength region, denoted R1, which can be the wavelength range [405,445] nm and a second wavelength region, which can be the wavelength region [460,500] nm, to analyze the spectrum recorded from a test specimen.

In one embodiment, a criterion for accepting a spectrum is that the computer 202 observes that the signal-to-noise ratio (SNR) for a spectrum is greater that a threshold, such as five(5). If the computer 202 determines that a spectrum, whether a reference spectrum or a test spectrum, has too small a SNR, the computer 202 rejects the spectrum. The computer 2020 accepts for analysis spectra that have suitable SNR values.

The computer 202 projects for each spectrum the spectral intensities in the selected regions, for example R1 and R2, onto the 2-dimensional space defined by $$S_{2d} = \left( \frac{1}{|bin_1(j)|} \cdot \sum_{\lambda \in bin_1(j)} S_A(\lambda), \frac{1}{|bin_2(k)|} \cdot \sum_{\lambda \in bin_2(k)} S_A(\lambda) \right).$$

In order to confirm the validity of the system and method, spectra representing tissue having known conditions of normal health and CIN II/III were analyzed by the computer 202. In one embodiment, for spectra having SNR>=5, the computer 202 separated the known spectra into the correct categories of normal health and CIN II/III with very high sensitivity and specificity (>80%).

In FIG. 9, the set of plotted points includes a point $s_{41}$ that has a very small value (of the order of $10^{-11}$) and several points, for example $s_{51}$, and $s_{62}$, that have considerably larger values, of the order of $10^{-8}$. In accordance with the above analysis, the computer 202 selects the spectral regions corresponding to $s_{41}$ for analysis, so as to best discriminate the two conditions of interest, in preference to using spectral regions corresponding to $s_{51}$ and $S_{62}$.

Figure 10:
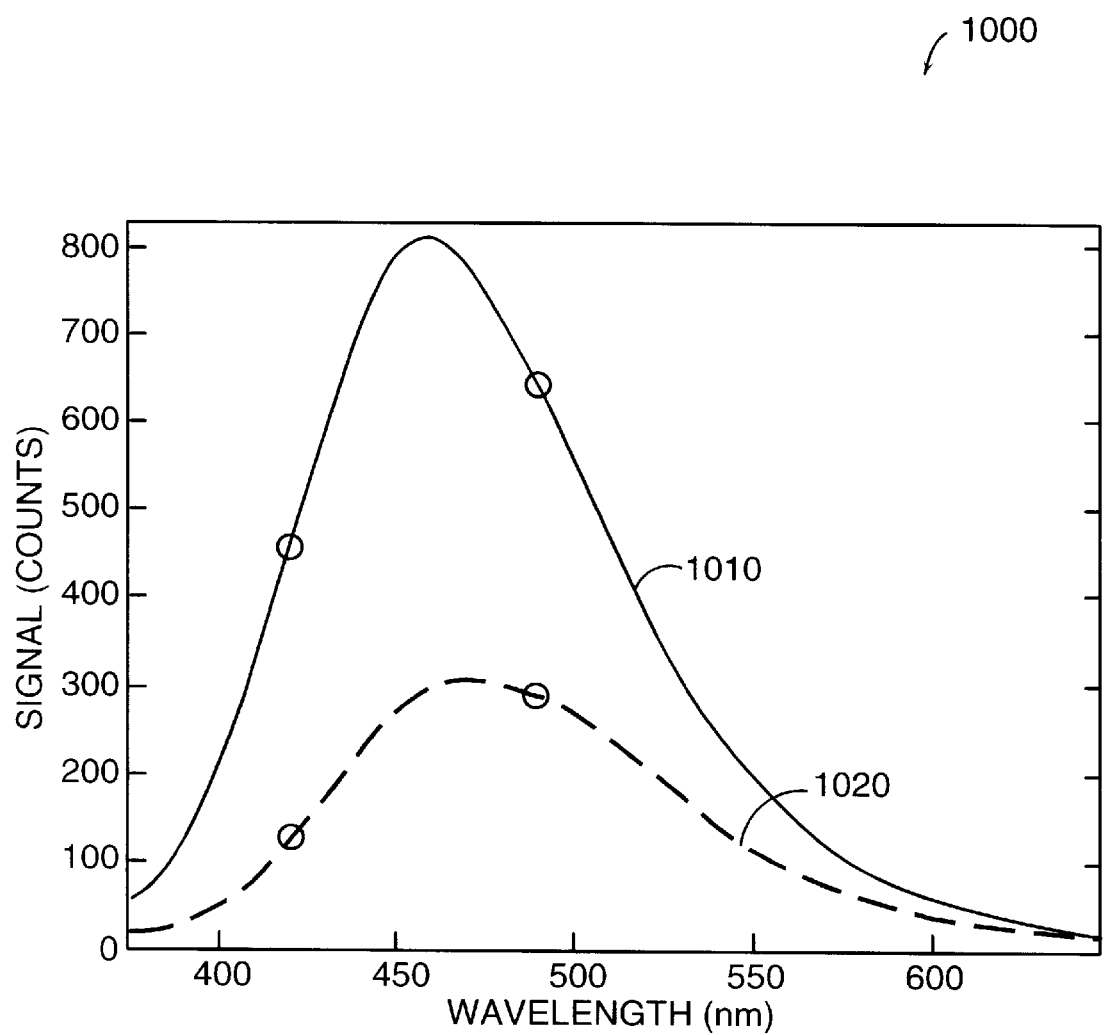
FIG. 10 is a graph showing two exemplary spectra having two regions of interest, according to an illustrative embodiment of the invention.

For the purposes of discussion, only two wavelengths will be considered as of interest in characterizing a spectrum from a test specimen. Those skilled in the spectroscopic arts will understand that a plurality of wavelengths can be employed, and that the precise number of such wavelengths will depend of the kind of information that is sought and the location of information within a spectrum. FIG. 10 is a graph 1000 showing two exemplary spectra 1010, 1020 having two regions of interest. In FIG. 10, a first exemplary amplitude is recorded for each spectrum 1010, 1020 at a wavelength of approximately 425 nm and a second exemplary amplitude is recorded for each spectrum 1010, 1020 at a wavelength of approximately 485 nm. In the illustrative example under discussion, the first spectrum becomes the ordered pair of numbers ($I_1(425)$, $I_1(485)$), and the second spectrum is represented by ($I_2(425)$, $I_2(485)$).

In the illustrative example, each spectrum is reduced to an ordered pair of numbers. The illustrative ordered pair can be used to plot the location of a point representative of the spectrum as a point in a two-dimensional space, in which the first number of the ordered pair is plotted along a first axis, and the second number of the ordered pair is plotted along a second axis. The ordered pair of numbers is used to locate the points for these two spectra, as shown in FIG. 11.

FIG. 11 is a graph 1100 depicting an exemplary plotting of two N-dimensional data points 1101, 1102, where N=2, for the spectra shown in FIG. 10. If the number of data point extracted from the spectra is greater than two, the number of dimensions in the space must be increased. While it is difficult to draw diagrams that show more than three dimensions, there is no problem generalizing the process to many dimensions, once the concept is understood. Those of skill in the arts associated with mathematical analysis will recognize that in general, a point corresponding to an ordered "k-tuple" can be plotted uniquely in an k-dimensional space, where the successive numbers of the ordered "k-tuple" are successively plotted against the k axes that define the k-dimensional space, where k is an integer greater than 0. In one embodiment, many dimensions are used for both the fluorescence spectra and the elastic backscatter spectra. In one embodiment, the number of dimensions used to represent a point corresponding to a spectrum does not have to be the same for the two types of spectra, because each type of spectrum can involve different information having different numbers of amplitudes that are required to represent the information. In other embodiments, equal numbers of amplitudes can be used to represent different types of spectra.

For reference spectra that correspond to reference specimens having known conditions, for example, conditions of health of cervical tissue that include normal health, metaplasia, CIN I, and CIN II/III, the points that are plotted in a multi-dimensional space often fall within regions of finite extent, or "constellations." In one embodiment, the result of the plotting process is a first cluster of points associated with state of health of cervical tissue, and another cluster (or neighborhood) for another state of health of cervical tissue. There is no a priori reason why there cannot be many different substantially localized clusters or neighborhoods or constellations in this multi-dimensional space state of health of cervical tissue, each state representative of a state of health of cervical tissue. This is not to say that there cannot be "outlying" points that are known to belong to a particular condition, that fall near to a constellation corresponding to a different condition.

In one embodiment, a sample size of greater than 25 is sufficient but not necessary to ensure accurate representation of the population of points in two-dimensional space (see, e.g., R. V. Hogg and E. A. Tanis at page 157). Once the neighborhoods of points representing reference spectra corresponding to tissue having known conditions have been established with a sufficient number of data points, the centroid of each neighborhood can be found.

FIG. 12 is a graph 1200 depicting an exemplary plotting of many N-dimensional data points for two sets 1201, 1202 of reference spectra, where N=2. As shown in FIG. 12, in an illustrative example given in two-dimensional space, the centroid is simply the average location for each constellation 1201, 1202 of data. The horizontal coordinate for a constellation corresponding to a specific state of health of cervical tissue is computed by finding the average of the horizontal coordinates for that particular constellation A similar averaging is done for the vertical coordinate.

Figure 13:
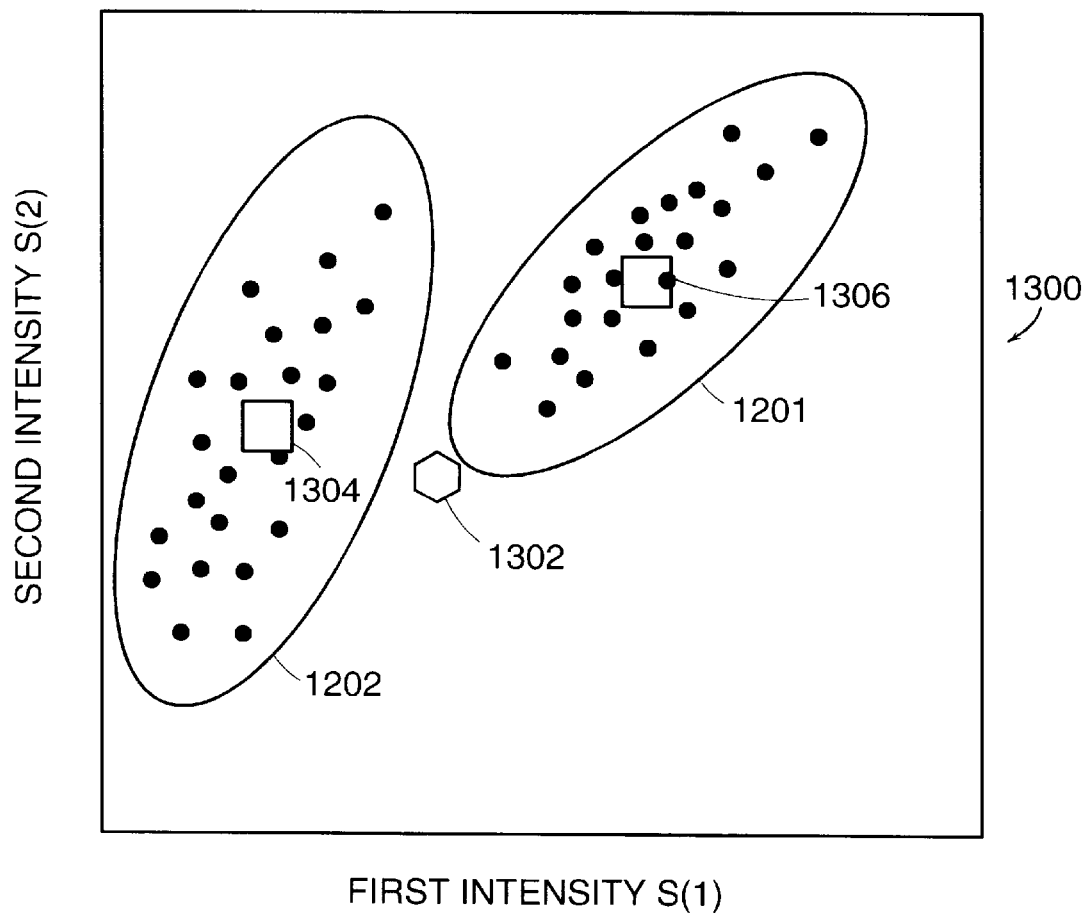
FIG. 13 is a graph depicting an exemplary plotting of many N-dimensional data points for two sets of reference spectra, where N=2, and an N-dimensional plot of a data point for an exemplary test spectrum, according to an illustrative embodiment of the invention.

FIG. 13 is a graph 1300 depicting an exemplary plotting of many N-dimensional data points 1201, 1202 for two sets of reference spectra, where N=2, and an N-dimensional plot of a data point 1302 for an exemplary test spectrum.

In one embodiment, a test spectrum recorded from a test specimen is classified by comparison with the reference spectra recorded from specimens having known conditions. The test spectrum corresponding to a specimen having an unknown condition is processed in exactly the same manner as the reference spectra are processed. The N-dimensional point for the unknown spectrum is plotted in the N-dimensional space, and its location is evaluated relative to the locations of the centroids of the neighborhoods of reference spectra. In an illustrative embodiment, this evaluation of location uses the Mahalanobis distance calculation.

FIG. 13 shows a point 1302 from an unknown tissue sample as a hexagonal point. Although it may be closer in the Euclidean sense to the centroid 1304 on its left than to the centroid 1306 above it, the Mahalanobis distance will actually show that it is "closer" to the class above it. Therefore, this unknown tissue spectrum will be classified as belonging to the class with the smaller Mahalanobis distance.

After a number of spectra from unknown tissue types have been examined in this manner, it is possible to score the process in terms of sensitivity and specificity. Sensitivity and specificity are calculated based on the number of spectra correctly classified. This is done during the algorithm development effort in order to find out if the process correctly classifies spectra, and can also be computed when the system and method are operating, to permit a check on the continued accuracy of a particular machine. The true classification of the "unknown" or test tissue specimen must in fact be known in order to make the evaluation of sensitivity and specificity. A standard test, such as a biopsy and analysis of a test specimen, can be performed to provide unambiguous data for the sensitivity and specificity analysis.

Figure 14:
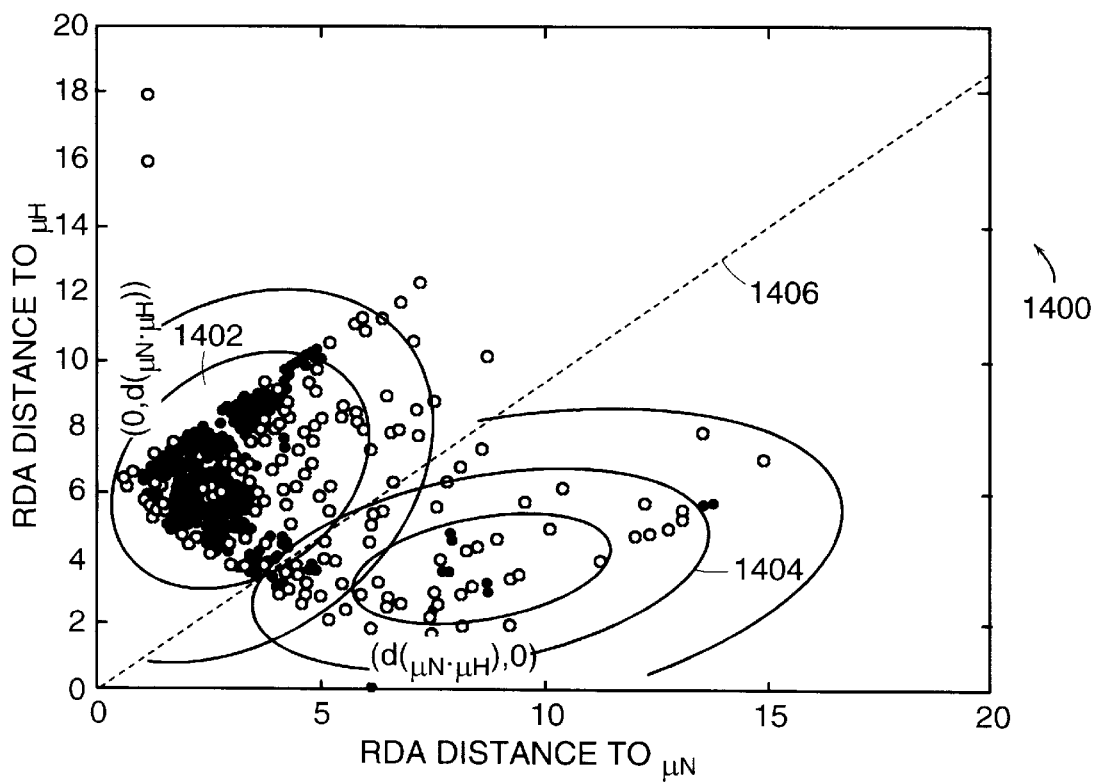
FIG. 14 is a graph of an exemplary 2-dimensional plot of two sets of reference spectral data, according to an illustrative embodiment of the invention.

FIG. 14 is a graph 1400 of an exemplary 2-dimensional plot of two sets 1402, 1404 of reference spectral data. The computer 202 performs the Mahalanobis distance calculation discussed in the previous section, and the Mahalanobis distances from unknown spectral points to the two centroids of the training set can be computed. Thus, for each unknown spectrum, a pair of distances is computed. These can be plotted on a two-dimensional plot to examine the quality of the separation between the tissue types.

FIG. 14 shows an example of such scatter plots, using fluorescence data for excitation at 355 nm. The discriminant line in FIG. 14 is a 45° line 1406, indicating that in one embodiment, the classification is strictly by minimum distance. For this example, the sensitivity is 0.92 and the specificity is 0.92. Any point falling above the line is classified as representing a spectrum of a specimen not having disease, while any point falling below the line is classified as representing a spectrum of a specimen having disease.

Other methods of placing the discriminant line have been examined. In one method, the computer 202 divides the data into a training set for finding the tissue centroids in the multidimensional space, a testing set to establish the scatter plot, and a validation set to determine algorithm performance. After the computer 202 establishes the neighborhoods and centroids using the training set, the computer 202 runs the testing set to establish the location of the discriminant line. One way for the computer 202 to position the line is to compute the average points for the two tissue types in the scatter plot, connect these average points with a straight line, and bisect this line with the discriminant line. This places a data-dependent bias onto the discriminant line. Without a doubt, this technique produces slightly better results as measured by sensitivity and specificity, but is deemed to be less objective than setting the 45° line.

Figure 15:
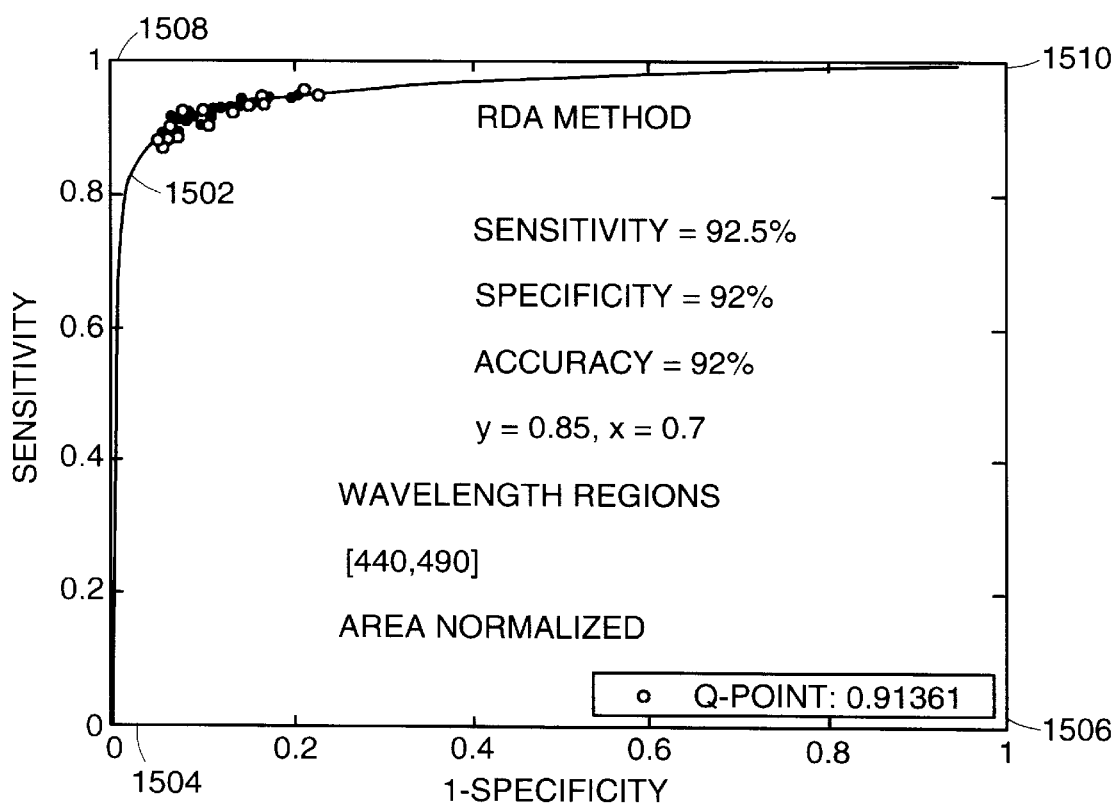
FIG. 15 is a graph of an exemplary ROC plot for categorization of tissue samples as normal squamous tissue or as tissue having CIN II/III lesions, according to an illustrative embodiment of the invention.

FIG. 15 is a graph 1500 of an exemplary ROC plot for categorization of tissue samples as normal squamous tissue or as tissue having CIN II/III lesions.

Classification results are reported in terms of true positives (those sites on the cervix with disease that have been identified as disease), true negatives (cervical sites without disease identified as being without disease), false positives (sites without disease identified as having disease), and false negatives (sites with disease but classified as being normal). The goal in any classification is to place the tissue correctly into the true positive and true negative categories, without classifying any tissue in the false positive or false negative categories.

The metrics of sensitivity and specificity are used to monitor classification results. Sensitivity is a measure of the number of diseased sites correctly identified as diseased, divided by the total number of truly diseased sites. Specificity is a measure of the number of normal tissue sites identified, divided by the total number of truly normal tissue sites. Both sensitivity and specificity work together to qualify a particular algorithm classification. For example, it is desirable to have an algorithm with high sensitivity, so the diseased tissue site are properly identified for further clinical processing. A device that calls all tissue sites as being diseased will have 100% sensitivity, because it does not miss any diseased sites. However, it will have 0% specificity, because it does not find any normal tissue sites. High sensitivity ensures that diseased sites are found and correctly classified, while high specificity guarantees that normal sites are not indicated for further treatment.

There is always a compromise between sensitivity and specificity in a classification algorithm. This is best demonstrated through the used of Receiver Operation Characteristics (ROC) curves developed to evaluate radar performance. In the ROC plot, sensitivity is plotted as the vertical axis, while one minus the specificity is plotted as the horizontal axis. Both axes extend from zero to one. A perfect algorithm, then would operate with 100% sensitivity and 100% specificity, placing the operation point at the upper left-hand corner of the ROC curve. This is the ideal operating point.

Real-world algorithms rarely operate at the ideal point on the ROC curve. FIG. 15 shows the ROC curve 1502 for discriminating between tissue exhibiting normal health and tissue exhibiting CIN II/III. A line drawn from the origin (the point 0,0) 1504 to the point (1,1) 1510, that is, a diagonal, is the line of pure chance (50%/50% classification). On the curve 1502, the point for which sensitivity and specificity are equal is called the Q-point of the ROC curve 1502. This point is the intersection of the ROC curve 1502 with a straight line drawn from the point (0,1) 1508 to the point (1,0) 1506. It is often convenient to report results of a classification by listing the Q-point on the associated ROC curve 1502. Another measure is the area under the curve 1502, where an area of 0.5 represents pure chance, and an area of 1.0 is perfect performance. For this exemplary embodiment, the Q-point is 0.91361 in FIG. 15.

In the foregoing, the system and method of the invention has been illustrated by recourse to a description given in terms of the Mahalanobis distance. Those of skill in the spectroscopic arts will recognize that other methods of categorizing a test spectrum by discriminating between a plurality of reference spectra can be used. For example, in addition to Mahalanobis distances, it is possible to employ Principal Component Analysis (PCA), Linear Discriminant Analysis (LDA), Quadratic Discriminant Analysis (QDA), Regularized Discriminant Analysis (RDA), and other methods.

By way of illustration, a computer 202 can project p-dimensional data into a coordinate system of dimension 2 or 3. As indicated above, the computer 202 can compute the data matrix for the $j^{th}$-tissue class $T_j$, using for example the four tissue classes defined above.

The task to be performed by the computer 202 is to select some subset $X_1$ of the reference data matrices and use this subset to classify spectra from test spectra obtained from specimens under test. $T_j$ is referred to as the Group Data Matrix and $T_j$ is associated with Group j, or class j.

$$T_j = \begin{bmatrix} T_j(1, \lambda_1) & T_j(2, \lambda_1) & \cdots & T_j(n_j, \lambda_1) \\ T_j(1, \lambda_2) & T_j(2, \lambda_2) & \cdots & T_j(n_j, \lambda_2) \\ \vdots & \vdots & \cdots & \vdots \\ T_j(1, \lambda_p) & T_j(2, \lambda_p) & \cdots & T_j(n_j, \lambda_p) \end{bmatrix} \quad (17)$$

$T_j$ is a $pxn_j$ matrix: $T_j \in Mat_{pxn_j}(K)$. $T_1 = N^T$ where N is defined as before. As described above, the computer 202 can define the group covariance matrix $\Sigma_j$, the group mean $\mu_j$, and the overall mean y.

$$\sum_j = cov(T_j) = \frac{1}{n_j - 1}(T_j - \langle T_j \rangle)(T_j - \langle T_j \rangle)^T \quad (18)$$

$1_{n_j} = (1,1, \ldots, 1) \in Mat_{1 \times n_j}(K)$ $$\langle T_j \rangle = \begin{bmatrix} \frac{1}{n_j} \sum_{k=1}^{n_j} T_j(k, \lambda_1) \cdot l_{n_j} \\ \frac{1}{n_j} \sum_{k=1}^{n_j} T_j(k, \lambda_2) \cdot l_{n_j} \\ \vdots \\ \frac{1}{n_j} \sum_{k=1}^{n_j} T_j(k, \lambda_p) \cdot l_{n_j} \end{bmatrix} = \begin{bmatrix} | & | & \cdots & | \\ \mu_k & \mu_k & \cdots & \mu_k \\ | & | & \cdots & | \end{bmatrix} \quad (19)$$

$$\mu_j = \left( \frac{1}{n_j} \sum_{k=1}^{n_j} T_j(k, \lambda_1), \frac{1}{n_j} \sum_{k=1}^{n_j} T_j(k, \lambda_2), \ldots, \frac{1}{n_j} \sum_{k=1}^{n_j} T_j(k, \lambda_p) \right)^T \in Mat_{px1}(\mathbb{R}) \quad (20)$$

$$y = \frac{1}{n} \sum_{i=1}^{g} n_j \mu_j, \text{ (g = number of tissue classes)} \quad (21)$$

As described before, the pooled within-groups covariance $\Sigma$ is the weighted average of the group covariance matrices.

$$\sum = \frac{1}{n-g} \sum_{j=1}^{g} (n_j - 1) \cdot \sum_j \quad (22)$$

The between-groups covariance matrix B is the outer product of the group means and the overall mean.

$$B = \frac{1}{g-1} \sum_{j=1}^{g} n_j (\mu_j - y)(\mu_j - y)^T \in Mat_{pxp}(\mathbb{R}) \quad (23)$$

The computer 202 can construct discriminant coordinates, as per Gnanadesikan, as follows. The computer 202 computes the Cholesky decomposition of $\Sigma$. The computer 202 uses the Cholesky algorithm, e.g., Demmel) to write $\Sigma$ as the product of upper triangular matrices: $\Sigma = U^T U$ and $$U = \begin{bmatrix} u_{11} & u_{12} & \cdots & u_{1p} \\ 0 & u_{22} & \cdots & u_{2p} \\ \vdots & \vdots & \cdots & \vdots \\ 0 & 0 & \cdots & u_{pp} \end{bmatrix}$$

is upper triangular. It is important to note that the Cholesky decomposition can be performed only on symmetric positive definite matrices. For the present analysis, one can further require $\Sigma$ to be of full rank.

The computer 202 sets $H=(U^{-1})^T B(U^{-1})=U^{-T}BU^{-1}$ and computes the Schur Decomposition of H. The computer 202 finds a diagonal matrix D and an orthogonal matrix Q so that $H=QDQ^T$ with $QQ^T=Q^TQ=I$. The computer 202 can assume that the diagonal elements $d_{jj}$ of D are such that $d_{11} \geq d_{22} \geq \ldots \geq d_{pp}$. If not, the computer 202 can sort D so that the diagonals are in descending order and rearrange the columns of Q to correspond to the changes in D.

The computer 202 sets $V=U^{-T}Q$. Then, $V^T \Sigma V=I$. Moreover, the diagonals of D are the eigenvalues of $\Sigma^{-1}B$. The computer 202 can select $r=max([2,min([g-1,p])])$. That is, the computer 202 can require $r \geq 2$ and $r \geq g-1$; typically, $p \gg g$. The computer 202 can then select $D_r$ to be the rxr sub-matrix composed of the first r rows and r columns of D and can select $V_r$ to be the rxp sub-matrix composed of the first r rows of V. Then $$A = \frac{1}{tr(D)} D_r V_r$$

is the projection matrix into discriminant coordinates and $$Z = AX \quad (24)$$

is the projection of the data matrix X into discriminant space, where X is given by.

$$X = \begin{bmatrix} T_1 \\ T_2 \\ \vdots \\ T_g \end{bmatrix} \quad (25)$$

$z(1), z(2), \ldots, z(r)$ are the discriminant coordinates, where $z(j)$ is the $j^{th}$-row of Z.

Equivalents

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for determining a condition of a test specimen, said method comprising, obtaining at least one optical spectrum from a test specimen, said optical spectrum being characterized by (N) quantitative features, each of said (N) quantitative features corresponding to one of (N) pre-selected wavelengths, wherein (N) is an integer greater than 1, determining a first metric between a point in N-dimensional space corresponding to said (N) quantitative features of said optical spectrum from said test specimen and a point in N-dimensional space characteristic of a first constellation of reference data comprising a first plurality of points in N-dimensional space, each of said first plurality of points corresponding to (N) quantitative features of a reference optical spectrum at said (N) pre-selected wavelengths, said first constellation of reference data being representative of a first known condition, determining a second metric between said point in N-dimensional space corresponding to said (N) quantitative features of said optical spectrum from said test specimen and a point in N-dimensional space characteristic of a second constellation of reference data comprising a second plurality of points in N-dimensional space, each of said second plurality of points corresponding to (N) quantitative features of a reference optical spectrum at said (N) pre-selected wavelengths, said second constellation of reference data being representative of a second known condition, and assigning one of said first and said second conditions to said test specimen, based at least in part on a relationship between said first and said second metrics.

2. The method of claim 1, wherein said first metric and said second metric each are selected from the group consisting of a square root of a sum of the squares of the differences of points in the N-dimensional space, a Mahalanobis distance, a Bhattacharyya distance, and a probability.

3. The method of claim 1, further comprising, providing said test specimen from a patient, obtaining said at least one optical spectrum from at least one of a fluorescence spectrum, a reflectance spectrum and a Raman spectrum, and assigning one of a first state of health of said tissue sample corresponding to said first known condition and a second state of health of said tissue sample corresponding to said second known condition.

4. The method of claim 3, wherein providing said test specimen comprises providing a specimen of human cervical tissue.

5. The method of claim 4, wherein providing a specimen of human cervical tissue comprises providing a specimen of human cervical tissue in vivo.

6. The method of claim 4, wherein said first state of health is normal health and said second state of health is a state of health a selected one of moderate cervical intraepithelial neoplasia (CIN II) and severe cervical intraepithelial neoplasia (CIN III).

7. The method of claim 1, further comprising, reporting that said optical spectrum is inconclusive with regard to said first known condition and said second known condition in response to each of said first and said second metrics exceeding a pre-determined metric value.

8. The method of claim 1, wherein at least one of said point in N-dimensional space characteristic of a first constellation of reference data and said point in N-dimensional space characteristic of a second constellation of reference data is one of a centroid of a respective one of said constellations of reference data and a weighted average of a respective one of said constellation of reference data.

9. The method of claim 1, wherein said quantitative features are selected from the group consisting of an amplitude, an average of a plurality of amplitudes, a function of a plurality of amplitudes, an average slope, a derivative, and an integral.

10. A method of determining that a condition of a test specimen belongs to one of a plurality of known conditions, each of said plurality of conditions represented by a reference specimen constellation corresponding to a selected one of the plurality of known conditions, the method comprising, obtaining at least one optical spectrum from a test specimen, selecting (N) quantitative features from said at least one optical spectrum, each of said (N) quantitative features being associated with one of (N) pre-selected wavelengths, wherein (N) is an integer greater than 1, determining a plurality of metric values, each metric value corresponding to a measure between a point in the N-dimensional space corresponding to said (N) quantitative features of the optical spectrum from the test spectrum and a point in N-dimensional space characteristic of a constellation of reference data representing a selected one of a plurality of known conditions, each said constellation comprising a plurality of points in the N-dimensional space, and deducing a condition to be ascribed to the test specimen based at least in part on the relation between the plurality of metric values.

11. The method claim 10, wherein at least one of the plurality of metrics is a distance, said distance being calculated as a selected one of a square root of a sum of the squares of the differences in the corresponding coordinates in the N-dimensional space, a Mahalanobis distance, and a Bhattacharyya distance.

12. The method claim 10, wherein at least one of the plurality of metrics is a probability.

13. The method of claim 10, further comprising, providing said test specimen from a patient, obtaining said at least one optical spectrum from at least one of a fluorescence spectrum, a reflectance spectrum and a Raman spectrum, and deducing one of a plurality of states of health to be ascribed to said tissue sample corresponding to a respective one of said plurality of known conditions.

14. The method of claim 13, wherein providing said test specimen comprises providing a specimen of human cervical tissue.

15. The method of claim 14, wherein providing a specimen of human cervical tissue comprises providing a specimen of human cervical tissue in vivo.

16. The method of claim 14, wherein said plurality of states of health comprises a state of health selected from the group consisting of normal health, normal squamous epithelium, columnar epithelium, immature metaplasia, mature metaplasia, Nabothian cysts, crypt openings, traumatically eroded tissue, benign polyps, mild cervical intraepithelial neoplasia (CIN I), moderate cervical intraepithelial neoplasia (CIN II), severe cervical intraepithelial neoplasia (CIN III) and cancer.

17. The method of claim 10, further comprising, reporting that said optical spectrum is inconclusive with regard to said plurality of known conditions in response to each of said plurality of metrics exceeding a pre-determined metric value.

18. The method of claim 10, wherein said point in N-dimensional space characteristic of a constellation of reference data representing a selected one of a plurality of known conditions is selected from the group consisting of a centroid of said constellations of reference data and a weighted average of said constellation of reference data.

19. The method of claim 10, wherein said quantitative features are selected from the group consisting of an amplitude, an average of a plurality of amplitudes, a function of a plurality of amplitudes, an average slope, a derivative, and an integral.

20. A system for determining a condition of a test specimen, comprising, a computer that receives data characteristic of at least one optical spectrum recorded from a test specimen, said data comprising (N) quantitative features of said optical spectrum, each of said (N) quantitative features corresponding to one of (N) pre-selected wavelengths, wherein (N) is an integer greater than 1, a first memory in communication with said computer and containing a first constellation of reference data comprising a first plurality of points in N-dimensional space, each of said first plurality of points corresponding to (N) quantitative features of a reference optical spectrum at said (N) pre-selected wavelengths, said first constellation of reference data being representative of a first known condition, a second memory in communication with said computer that contains a second constellation of reference data comprising a second plurality of points in N-dimensional space, each of said second plurality of points corresponding to (N) quantitative features of a reference optical spectrum at said (N) pre-selected wavelengths, said second constellation of reference data being representative of a second known condition, said computer adapted to determine a first metric between a point in N-dimensional space corresponding to said (N) quantitative features of said optical spectrum from said test specimen and a point in N-dimensional space characteristic of said first constellation of reference data, said computer adapted to determine a second metric between said point in N-dimensional space corresponding to said (N) quantitative features of said optical spectrum from said test specimen and a point in N-dimensional space characteristic of said second constellation of reference data, and said computer adapted to assign one of said first and said second conditions to said test specimen, based at least in part on a relationship between said first and said second metric values.

21. The system according to claim 20, wherein said first distance and said second metrics each are selected from the group consisting of a square root of a sum of the squares of the differences in coordinates of points in the N-dimensional space, a Mahalanobis distance, and a Bhattacharyya distance.

22. The system according to claim 20, wherein said test specimen is a tissue sample and said first and said second conditions correspond to states of health.

23. The system according to claim 22, wherein said tissue sample comprises human cervical tissue, said first state of health and said second state of health are selected from the group consisting of normal health, normal squamous epithelium, columnar epithelium, immature metaplasia, mature metaplasia, Nabothian cysts, crypt openings, traumatically eroded tissue, benign polyps, mild cervical intraepithelial neoplasia (CIN I), moderate cervical intraepithelial neoplasia (CIN II), severe cervical intraepithelial neoplasia (CIN III) and cancer.

24. The system according to claim 20, wherein said computer is further adapted to report that said data characteristic of said optical spectrum recorded from said test specimen is inconclusive as regards said first known condition and said second known condition in response to said first and said second distances both exceeding a pre-determined metric.

25. The system according to claim 20, wherein said computer is further adapted to compute as one of said point in N-dimensional space characteristic of a first constellation of reference data and said point in N-dimensional space characteristic of a second constellation of reference data a point selected from the group consisting of a centroid of said constellation of reference data and a weighted average of said constellation of reference data.

26. The system according to claim 20, wherein said at least one optical spectrum recorded from a test specimen comprises an optical spectrum selected from the group consisting of a fluorescence spectrum, a reflectance spectrum and a Raman spectrum.

27. The system according to 20, wherein at least one of said point in N-dimensional space characteristic of a constellation of reference data representing a selected one of a plurality of known conditions is selected from the group consisting of a centroid of said constellation of reference data and a weighted average of said constellation of reference data.

28. The system according to claim 20, wherein said test specimen comprises human tissue.

29. The system according to claim 28, wherein said first and said second known conditions are selected from the group consisting of healthy tissue, inflammation of tissue, atrophic tissue, hypoxic tissue, diseased tissue, and cancerous tissue.

* * * * *